United States Patent
Vayser et al.

(10) Patent No.: US 8,899,809 B2
(45) Date of Patent: Dec. 2, 2014

(54) ILLUMINATED CLIP AND METHODS OF USE

(71) Applicant: Invuity, Inc., San Francisco, CA (US)

(72) Inventors: Alex Vayser, Mission Viejo, CA (US); Anant Hegde, Hayward, CA (US); Douglas Rimer, Los Altos Hills, CA (US)

(73) Assignee: Invuity, Inc., San Francisco, CA (US)

( * ) Notice: Subject to any disclaimer, the term of this patent is extended or adjusted under 35 U.S.C. 154(b) by 0 days.

(21) Appl. No.: 13/749,485

(22) Filed: Jan. 24, 2013

(65) Prior Publication Data

US 2014/0133173 A1    May 15, 2014

Related U.S. Application Data

(60) Provisional application No. 61/592,104, filed on Jan. 30, 2012.

(51) Int. Cl.

| | |
|---|---|
| *F21V 5/00* | (2006.01) |
| *G02B 6/06* | (2006.01) |
| *F21V 33/00* | (2006.01) |
| *A61B 17/02* | (2006.01) |
| *F21V 8/00* | (2006.01) |
| *A61B 19/00* | (2006.01) |

(52) U.S. Cl.
CPC ..... *F21V 33/0068* (2013.01); *A61B 2019/5206* (2013.01); *A61B 17/0206* (2013.01); *G02B 6/0001* (2013.01); *A61B 2217/005* (2013.01)
USPC .......................................... 362/572; 600/245

(58) Field of Classification Search
USPC ............................. 362/572; 385/901; 600/245
See application file for complete search history.

(56) References Cited

U.S. PATENT DOCUMENTS

| | | |
|---|---|---|
| 3,638,644 A | 2/1972 | Reick |
| 3,641,332 A | 2/1972 | Reick et al. |
| 3,890,960 A | 6/1975 | Wunsch et al. |
| 4,226,228 A | 10/1980 | Shin et al. |
| 4,562,832 A | 1/1986 | Wilder et al. |
| 4,592,344 A | 6/1986 | Scheer |

(Continued)

FOREIGN PATENT DOCUMENTS

| | | |
|---|---|---|
| EP | 0101781 A1 | 3/1984 |
| GB | 2078526 A | 1/1982 |

OTHER PUBLICATIONS

International search report and written opinion dated Mar. 28, 2013 for PCT/US2013/023871.

*Primary Examiner* — Stephen F Husar
(74) *Attorney, Agent, or Firm* — Wilson Sonsini Goodrich & Rosati

(57) ABSTRACT

A surgical clip for illuminating tissue in a surgical field has first and second elongate arms and a connector joining the arms together. The arms are biased to expand laterally outward into an expanded configuration in which the arms engage the tissue in the surgical field with enough force to seat the clip without retracting the tissue. A waveguide illuminator is coupled to the first arm, and has a light input portion, a light output portion, and a light conducting portion extending between the light input portion and the light output portion. Light passes through the waveguide illuminator by total internal reflection, and the waveguide illuminator directs light to the tissue. Methods of using the illuminated clip are also disclosed.

55 Claims, 21 Drawing Sheets

(56) References Cited

U.S. PATENT DOCUMENTS

| | | |
|---|---|---|
| 4,597,030 A | 6/1986 | Brody et al. |
| 4,605,990 A | 8/1986 | Wilder et al. |
| 4,643,172 A | 2/1987 | Taff et al. |
| 4,697,578 A | 10/1987 | Burgin |
| 4,807,599 A | 2/1989 | Robinson et al. |
| 4,842,356 A | 6/1989 | Mori |
| 4,961,617 A | 10/1990 | Shahidi et al. |
| 5,035,232 A | 7/1991 | Lutze et al. |
| 5,353,786 A | 10/1994 | Wilk |
| 6,120,436 A | 9/2000 | Anderson et al. |
| 6,185,356 B1 | 2/2001 | Parker et al. |
| 6,504,985 B2 | 1/2003 | Parker et al. |
| 7,306,559 B2 | 12/2007 | Williams |
| 7,871,375 B2 | 1/2011 | Talieh |
| 7,959,651 B2 | 6/2011 | Branch et al. |
| 8,012,089 B2 | 9/2011 | Bayat |
| 2006/0229593 A1 | 10/2006 | Vayser et al. |
| 2007/0060795 A1 | 3/2007 | Vayser et al. |
| 2007/0081358 A1 | 4/2007 | Shea et al. |
| 2008/0002426 A1 | 1/2008 | Vayser et al. |
| 2009/0105547 A1 | 4/2009 | Vayser et al. |
| 2010/0317928 A1 | 12/2010 | Subramaniam |
| 2011/0319720 A1 | 12/2011 | Grey et al. |
| 2012/0041268 A1* | 2/2012 | Grey et al. .................. 600/245 |

* cited by examiner

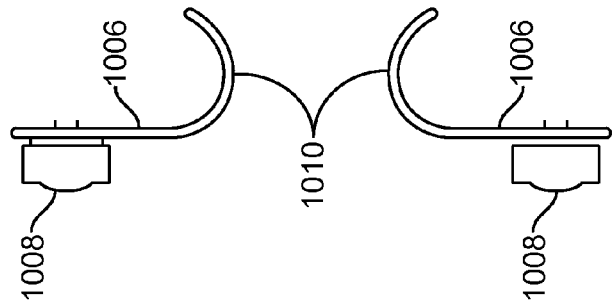
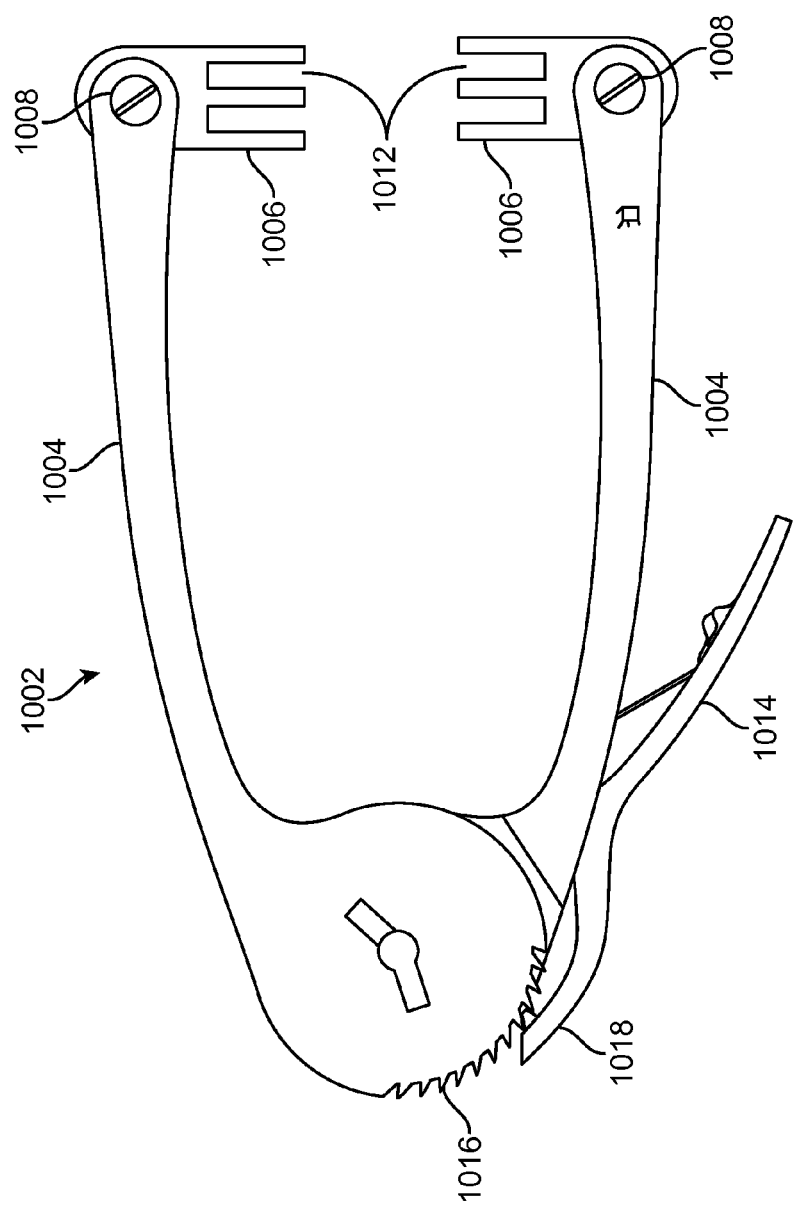
FIG. 10B
FIG. 10A

ILLUMINATED CLIP AND METHODS OF USE

CROSS-REFERENCE

The present application is a non-provisional of, and claims the benefit of U.S. Provisional Patent Application No. 61/592,104 filed Jan. 30, 2012; the entire contents of which are incorporated herein by reference.

BACKGROUND OF THE INVENTION

Illumination of body cavities for diagnosis and/or therapy is typically provided by overhead lighting or by headlamps. These forms of illumination can be challenging to use under certain situations. For example, overhead lighting must constantly be adjusted as the physician's position changes relative to the patient, as well as to illuminate different parts of the surgical field. Also, overhead lighting devices may require sterile handles to be attached to the lights in order for the physician to make adjustments without breaching the sterile field. Even then, the light provided by the overhead lamp may not illuminate the work space adequately. Head lamps can be heavy and uncomfortable to use, may require an assistant to help a physician put the headlamp on, and they often generate considerable amounts of heat during use which further limits comfort and can cause burns if an operator accidently mishandles the head lamp. Head lamps also require the physician to constantly adjust head position in order to illuminate the work space, and this can be uncomfortable to the physician.

In an attempt to address some of these issues, surgical instruments such as retractors have been coupled with light pipes such as fiber optics to conduct light from a light source such as a halogen light or a LED light source in order to illuminate a surgical field. For example, some conventional illuminated soft tissue retractors utilize a fiber optic light bundle attached to a retractor handle. The fiber optic bundle provides a very focused light and generates a significant amount of heat. The fiber optics tube is also typically in the line of sight of the user, thereby obstructing a surgeon's view in use. Also, the fiber optic bundle only provides a narrow spot of light and must be constantly adjusted to illuminate the surgical field and minimize glare or shadows. Additionally, the fiber optic bundle requires precision manufacturing and polishing, and the fibers are fragile and can be easily scratched, occluded by blood or other debris, or otherwise damaged in use. Thus fiber optic bundles can also be challenging to use in illuminated surgical systems.

Other materials may be used as waveguides that overcome some of the challenges associated with fiber optic bundles. Exemplary materials such as acrylic or polycarbonate have also been used as waveguides, but these materials have unstable light transmission characteristics under extended use, and the transmission characteristics may change after sterilization using convention techniques. For example, many polymers cross-link and yellow or become brittle after terminal sterilization with radiation. Heat from autoclaving or ethylene oxide sterilization can deform the waveguide. Additionally, precision optical polymers have limited mechanical properties which can limit their use in medical and surgical procedures. For example, some polymers are brittle and can easily shatter during use, or are difficult to process during manufacturing (e.g. hard to injection mold).

In addition to some of the challenges with illumination of a surgical field, surgical instruments such as retractor blades do not always accommodate the anatomy being treated, and the retractor blade and illumination device coupled to the retractor takes up precious space in the surgical field Therefore, it would be desirable to provide improved illuminated medical devices that provide better illumination of a work space and that reduce or eliminate some of the weight and heat constraints of traditional headlamps and overhead lighting. Such devices conform to the anatomy being treated, are easy to place, and have low profile so they do not take up significant amounts of space, thereby allowing more room for a surgeon's hand or other surgical instruments, and avoiding obstruction of the work space. Additionally, it would be desirable to provide such devices that provide superior lighting to allow visualization of the surgical field, including adjacent tissues such as nerves or blood vessels. Such devices preferably are easy to manufacture, may be single-use or re-sterilizable, and have desired mechanical properties in service. Such instruments also have low profiles so the instrument can fit through small incisions or be positioned in small surgical fields which reduce scarring, improve healing time, and reduce hospital stay. At least some of these objectives will be addressed by the embodiments disclosed herein.

SUMMARY OF THE INVENTION

The present invention generally relates to medical devices and methods, and more particularly relates to illuminated medical devices and methods.

In a first embodiment, a surgical clip for illuminating tissue in a surgical field comprises first and second elongate arms joined together with a connector element. The arms are biased to expand laterally outward into an expanded configuration. In the expanded configuration the first and second arms expand into engagement with the tissue in the surgical field with enough force to seat the clip without retracting the tissue. The surgical clip also includes a waveguide illuminator coupled to the first arm. The waveguide illuminator has a light input portion, a light output portion, and a light conducting portion extending between the light input portion and the light output portion. Light passes through the waveguide illuminator by total internal reflection, and the waveguide illuminator directs light to the tissue in the surgical field.

The first arm may have a proximal portion and a distal portion, and the proximal portion may be biased to preferentially flex in a first direction. The distal portion may be biased to preferentially flex in a second direction transverse to the first direction. The proximal portion may be twisted relative to the distal portion. The clip may also include a waveguide connector element coupled to the first arm. The waveguide connector element may be used to releasably couple the waveguide illuminator to the first arm. The waveguide connector element may be a snap fitting. The first arm may also have a pivoting mechanism for adjusting pitch of the waveguide illuminator. The pivoting mechanism may comprise a splined shaft that is operatively coupled to one of the first arm or the waveguide illuminator, and a receptacle for receiving the splined shaft operatively coupled with the other of the first arm or the waveguide illuminator.

The clip may also have a second arm that may have a proximal portion and a distal portion, where the proximal portion may be biased to preferentially flex in a first direction, and the distal portion may be biased to preferentially flex in a second direction transverse to the first direction. The proximal portion may be twisted relative to the distal portion. The clip may also have a second waveguide illuminator and a second waveguide connector element coupled to the second arm. The waveguide connector element may be releasably coupled with the second waveguide illuminator thereby releasably coupling the second waveguide illuminator with the second arm. The waveguide connector element may be a snap fitting. The second arm may also comprise a pivoting mechanism for adjusting pitch of the second waveguide illuminator. The pivoting mechanism may comprise a splined shaft operatively coupled to one of the second arm or the second waveguide illuminator, and a receptacle for receiving the splined shaft operatively coupled with the other of the second arm or the second waveguide illuminator.

The connector element may comprise a U-shaped element and may comprise a spring.

The waveguide illuminator may comprise a shield disposed thereover. The shield may be adapted to prevent glare from shining back into a physician's eyes, and the shield may also be adapted to prevent scratching or damage to the waveguide by other surgical instruments. The shield may further comprise a collar that may be disposed around the light input portion of the waveguide illuminator with an air gap therebetween. The air gap may be circumferentially disposed around the light input portion of the waveguide illuminator. The clip may also comprise a rear shield or backing element that may be coupled to the waveguide illuminator such that an air gap is disposed therebetween. The backing element may be adapted to reduce or prevent tissue or body fluids from contacting a rear surface of the waveguide illuminator. The waveguide illuminator may comprise active zones and dead zones, and light passes through the active zones by total internal reflection, and no light or substantially no light passes through the dead zones by total internal reflection.

The light input portion of the waveguide may similarly comprise active zones and dead zones. Light passes through the active zones by total internal reflection, and no light or substantially no light passes through the dead zones by total internal reflection. The light input portion may comprise a cylindrical proximal portion adapted to be coupled with a light source, and a rectangular distal portion optically coupled with the light conducting portion of the waveguide. The light output portion of the waveguide illuminator may comprise a plurality of surface features for extracting light from the waveguide illuminator and directing the extracted light laterally or distally toward the tissue in the surgical field. The surface features may comprise parallel prism shapes with a primary facet and a secondary facet.

The clip may further comprise a spring coupled with the connector element, and the spring may be biased to expand laterally outward. The spring may facilitate expansion of the first and second arms laterally outward away from one another. The clip may further comprise an engagement element coupled with the first arm, the second arm, or with the connector element, and the engagement element may capture the spring. The engagement element may comprise a central channel that extends at least partially therethrough and that is sized to receive the spring. The surgical clip may further comprise one or more anchoring elements that are coupled to either the first or the second elongate arm. The anchoring elements may comprise teeth. The surgical clip may also comprise means for evacuating smoke or fumes from the surgical field. The means for evacuating smoke may comprise a suction tube. The clip may comprise a locking mechanism that locks the first and second arms into a desired position relative to one another. The first arm may move parallel relative to the second arm.

In another aspect of the present invention, a method of illuminating a surgical field comprises providing a clip having a first arm, a second arm and a waveguide illuminator coupled to the first or second arm. Applying a force to one or more of the first and second arms moves the arms laterally inward toward one another into a collapsed configuration so that the clip may be positioned into the surgical field in the collapsed configuration. Releasing the force from the one or more arms allows the arms to move laterally outward into an expanded configuration so that the arms engage tissue in the surgical field. This seats the clip in the surgical field which can then be illuminated with light extracted from the waveguide illuminator.

The waveguide illuminator may comprise a light input portion, a light output portion, and a light conducting portion extending between the light input portion and the light output portion. The light may pass through the waveguide illuminator by total internal reflection, and the waveguide illuminator may direct light to the tissue in the surgical field. The light input portion of the waveguide may comprise active zones and dead zones. Light passes through the active zones by total internal reflection, and no light or substantially no light passes through the dead zones by total internal reflection.

Applying the force to the arms may comprise pressing or squeezing the first and second arms inward toward one another. The first and second arms may move parallel to one another. Positioning the clip may comprise advancing the clip into the surgical field. Releasing the force from the arms of the clip may comprise releasing the first or the second arm from an operator's grasp. Seating the clip may comprise engaging the arms of the clip against tissue in the surgical field so the clip remains stationary and without retracting the tissue. Illuminating the surgical field may comprise extracting light from the waveguide illuminator with a plurality of surface features on the waveguide illuminator and directing the extracted light laterally or distally toward the surgical field.

The method may further comprise releasably engaging the waveguide illuminator with the first or second arm. The waveguide illuminator may be detached from the first or the second arm. Also, the pitch of the waveguide illuminator relative to the first or second arm may be adjusted. The method may comprise anchoring the clip in the surgical field with teeth or with other anchoring elements. The method may also comprise evacuating smoke or fumes from the surgical field. The method may also comprise locking the clip so that the first arm maintains its position relative to the second arm.

In still another aspect of the present invention, a surgical clip for illuminating tissue in a surgical field comprises a first elongate arm, a second elongate arm and a connector element joining the first and second elongate arms. The arms are biased to expand laterally outward into an expanded configuration. In the expanded configuration the first and second arms expand into engagement with the tissue in the surgical field with enough force to seat the clip without retracting the tissue. One or more lights are coupled to the first elongate arm or the second elongate arm. The lights illuminate the surgical field.

The lights may comprise LEDs. The surgical clip may further comprise one or more anchoring elements coupled to either the first or the second elongate arm. The anchoring elements may comprise teeth. The surgical clip may further comprise means for evacuating smoke or fumes from the surgical field. The means for evacuating smoke comprises a suction tube.

In another aspect of the present invention, a surgical clip for illuminating tissue in a surgical field comprises a first elongate arm, a second elongate arm, and a connector element joining the first and second elongate arms. The arms are biased to expand laterally outward into an expanded configuration. In the expanded configuration the first and second arms expand into engagement with the tissue in the surgical field with enough force to seat the clip without retracting the tissue. The construct of the first elongate arm, the second elongate arm and the connector element form an optical waveguide. The first elongate arm or the second elongate arm comprise light extraction structures for extracting light therefrom and for directing light to the surgical field. The optical waveguide is formed from a single homogeneous material, and light is transmitted therethrough by total internal reflection.

These and other aspects and advantages of the invention are evident in the description which follows and in the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 10A-10B illustrate yet another embodiment of an illuminated clip.

DETAILED DESCRIPTION OF THE INVENTION

Figure 1A:
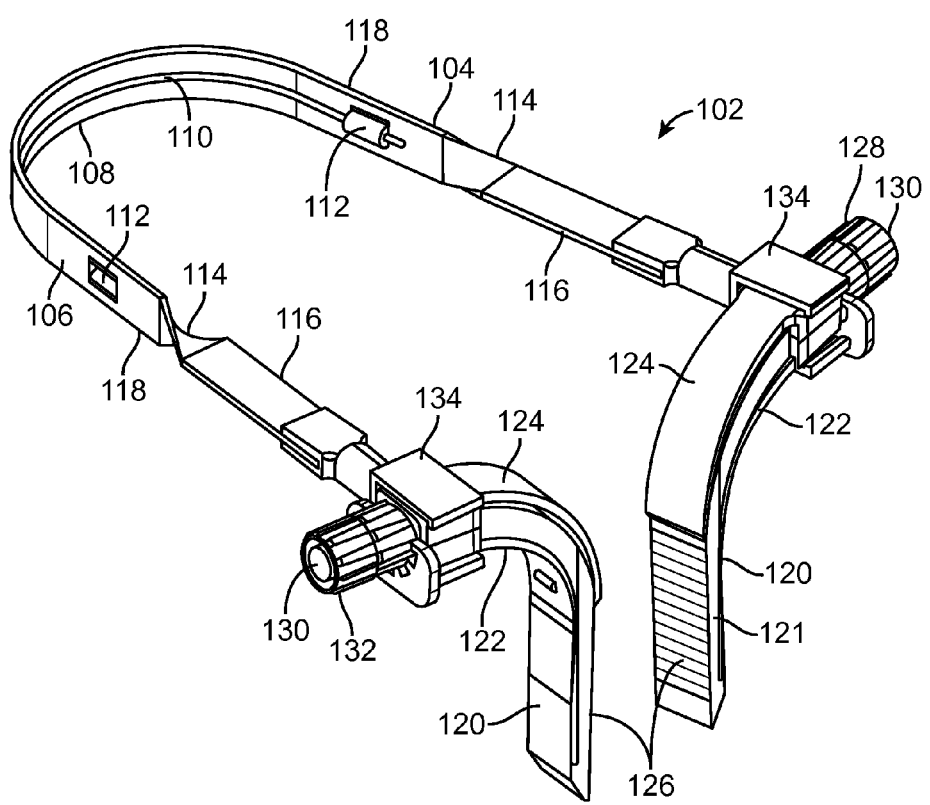
FIG. 1A illustrates a perspective view of an exemplary embodiment of an illuminated clip.

FIGS. 1A-1D illustrate an exemplary embodiment of an illuminated clip that may be used to illuminate a work area such as a surgical field. FIG. 1A shows a perspective view of the illuminated clip 102 which has a first arm 104 and a second arm 106. A connector element 108 joins the arms together to form the clip. An optional spring 110 may be coupled to the connector element 108 and the spring may also be coupled to the arms 104, 106 with an engagement element 112. A waveguide illuminator 120 is held by snap fitting 134 or with another coupling mechanism thereby coupling the waveguide illuminator 120 with the arms 104, 106. The waveguide illuminator may optionally include a shield 124 disposed over a front surface of the waveguide illuminator 120 and also optionally a backplate or backing element 122 disposed over a back surface of the waveguide illuminator 120. A collar 128 may be disposed over the light input portion 130 of the waveguide illuminator, and the waveguide illuminator also includes surface features 126 which extract light from the waveguide illuminator 120 and direct light to the surgical field.

The arms 104, 106 have a rectangular cross-section in this embodiment, but other cross-sections may also be used, including square, round, etc. One particular advantage of using a rectangular cross-section for the arms is that the arms will be biased to preferentially flex in one direction as opposed to an arm having a cross-section that is symmetrical in all directions and thus will not preferentially flex in one direction. Thus, in this exemplary embodiment, the arms include a proximal portion 116 and a distal portion 118. The proximal portion has the arm oriented in a first direction such that the arm is biased to preferentially flex in one direction, and the distal portion of the arm is oriented in a second direction such that the arm is biased to preferentially flex in a second direction transverse to the first direction. In this embodiment, the proximal portion of the arm preferentially flexes vertically up and down, and is twisted 114 relative to the distal portion of the arm 118 which preferentially flexes laterally inward and outward. Here the twisting is about 90 degrees. This configuration allows the arms to preferentially flex laterally (e.g. inward and outward) as well as vertically (upward and downward), and thus also the arms will have greater stiffness in one direction than the other. For example, the proximal portion of the arm will have greater stiffness in the lateral direction (inward and outward) as compared to the vertical direction (up and down). The converse is also true for the distal portion of the arm which will have greater stiffness in the vertical direction (up and down) than the lateral direction (inward and outward). Adjusting the length of the arms allows the stiffness of the arms to be controlled, thereby controlling arm deflection when a force is applied to the arms. Basic beam bending theory may be applied to estimate deflection under loading.

The connector element 108 joins the arms 104, 106 thereby forming a U-shaped clip. The connector element may be U-shaped and acts as a spring to allow the arms to flex inward or outward. In preferred embodiments, the arms and connector element are biased so that the arms extend laterally outward from one another into an expanded configuration or splayed geometry. Applying a force to the arms flexes the arms laterally inward toward one another to form a collapsed configuration. The material properties and dimensions of the connector element 108 and arms 104, 106 determine the stiffness of the clip. For example, the connector element 108 may act as a spring to control the deflection of the arms, or the arms themselves may act as leaf springs and control their deflection, or a combination of the two may control deflection. The connector element and arms may be fabricated using metals such as stainless steel, nitinol, a resilient polymer, or other materials may also be used. A supplemental spring 110 may be coupled to the clip using engagement elements 112 to provide additional spring force to the clip. In alternative embodiments, the connector element and arms may be a malleable material and the supplemental spring may provide the expansion force. Engagement elements 112 may be punched out or stamped regions of arms 104, 106 having a central channel extending therethrough for receiving the spring 110. In other embodiments, the supplemental spring 110 may be bonded, welded, snap fit, press fit, or otherwise coupled to the arms. The spring force of the clip may be designed to be any desired force. In preferred embodiments, the clip will spring outward with enough force so that the arms 104, 106 expand laterally outward into engagement with tissue in the surgical field. Similarly, the waveguide illuminators 120 will also expand laterally outward into engagement with tissue in the surgical field. The expansion has enough force so that the clip seats itself into engagement with the tissue in the surgical field or against other surgical instruments such as retractor blades already in the surgical field and holds the clip in place without sliding out of position or canting. Also, preferably the force exerted by the clip is insufficient to retract tissue. However, one of skill in the art will appreciate that the clip may have any force.

The waveguide illuminator 120 is preferably releasably coupled to the arms 104, 106 with a coupling element 134 such as a snap fit or other coupling mechanism. While this embodiment describes the use of a waveguide illuminator on each arm, in alternative embodiments only a single waveguide illuminator may be coupled to a single arm. The waveguide illuminator may also be moved from one arm to the opposite arm in order to adjust the field of illumination. Light from a light source (not shown) is introduced to the waveguide illuminator 120 at a light input portion 130 and the light then travels through a light transmitting portion 121 and then light is extracted from a light output portion which preferably includes a plurality of surface features or microstructures 126. These surface features may include facets, lenses or other features described herein or known to those of skill in the art. The light travels through the waveguide illuminator by total internal reflection, and light is then extracted from the waveguide with the microstructures 126 which direct the light laterally and distally away from the waveguide illuminator to illuminate tissue in the surgical field. An optional shield 124 may be disposed over a top or front surface of the waveguide illuminator. The shield 124 prevents other tools or surgical instruments from damaging the waveguide illuminator, and the shield also prevents glare from shining back into a physician's eyes. Preferably, an air gap is disposed between the shield and the waveguide illuminator in order to prevent light from leaking out of the waveguide illuminator. A backplate or backing element 122 may also optionally be disposed against a back or bottom surface of the waveguide illuminator. This helps to prevent blood or other tissue from contacting the waveguide illuminator which would cause light to leak out of the waveguide illuminator. Similarly, an air gap may be disposed between the backplate and the back surface of the waveguide illuminator to prevent light loss therebetween. Light input portion 130 is also preferably covered with a collar 128. The collar also may be used to form a fitting for engaging the light input portion of the waveguide illuminator with a light source. An air gap is disposed circumferentially around the light input portion in order to keep light from leaking out of the light input portion. Additional details about the waveguide illuminator are disclosed below. The waveguide illuminator may also be adjustable in order to control pitch (also referred to as toe-in or toe-out) and this is best illustrated in FIGS. 1C-1D.

Figure 1B:
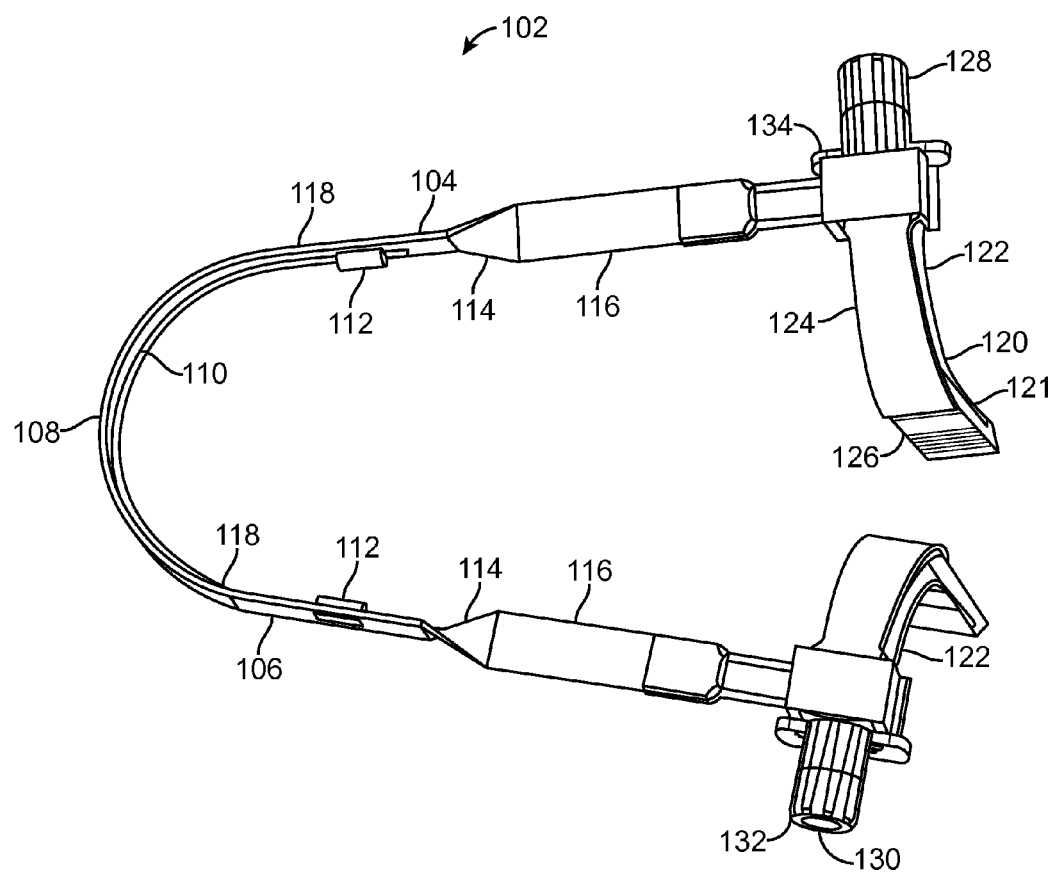
FIG. 1B illustrates a top view of the embodiment in FIG. 1A.
Figure 1C:
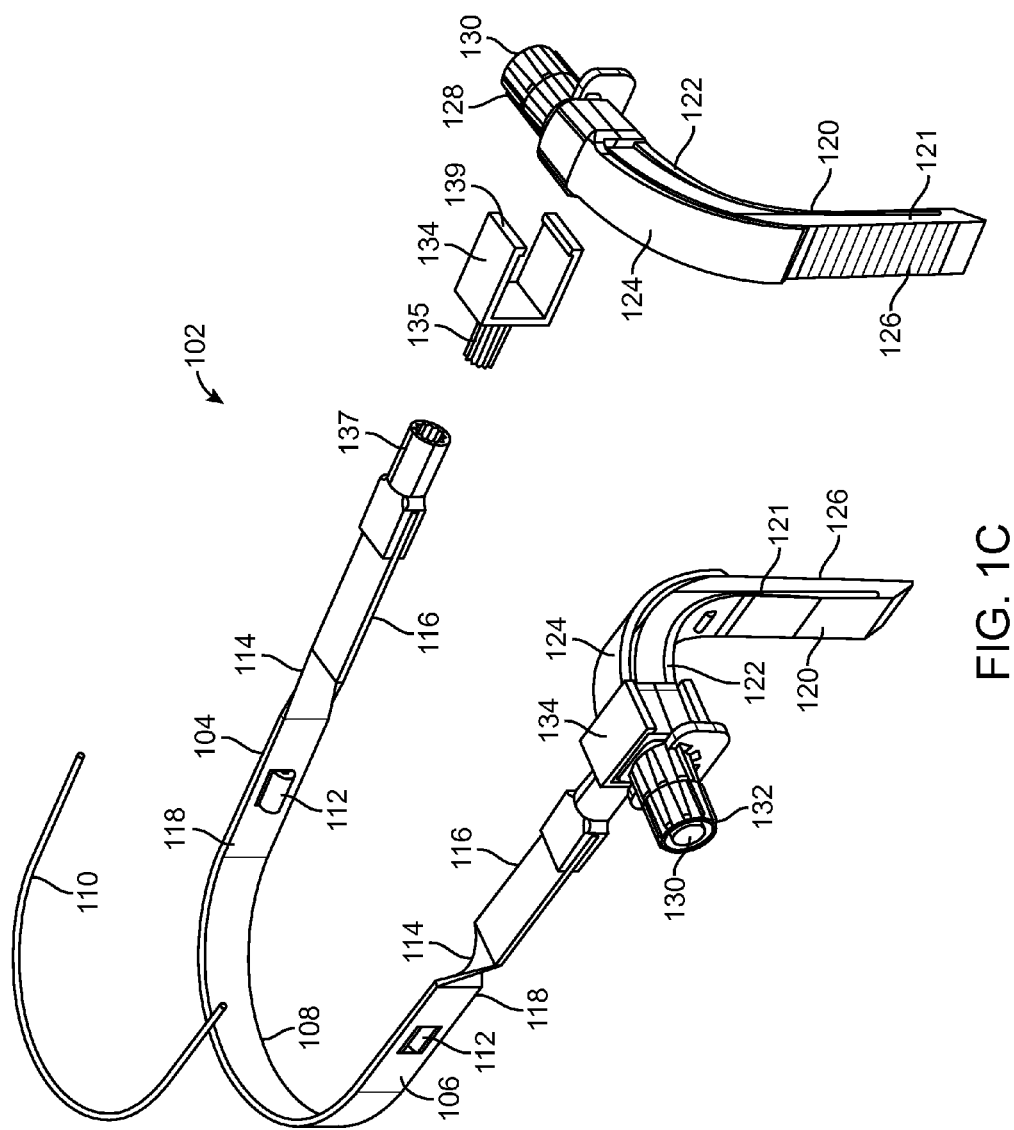
FIG. 1C illustrates a partially exploded perspective view of the embodiment in FIG. 1A.
Figure 1D:
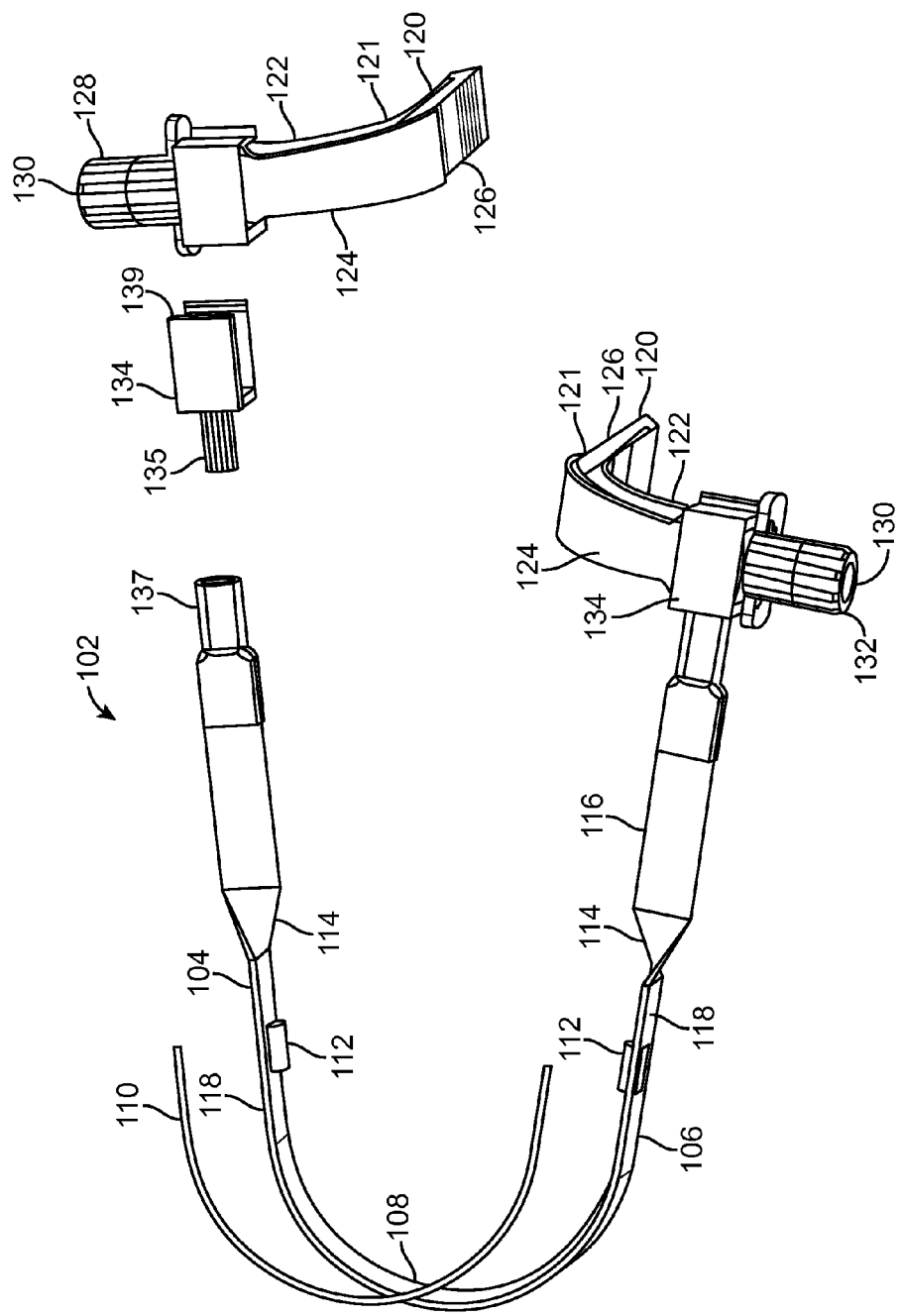
FIG. 1D illustrates a top view of FIG. 1C.

FIG. 1B illustrates a top view of the illuminated clip 102 seen in FIG. 1A. FIG. 1C is a partially exploded perspective view of the spring clip 102. FIG. 1C more clearly illustrates the pivoting mechanism for adjusting the pitch of the waveguide illuminator 120. The coupling element 134 which holds waveguide illuminator 120 has a splined shaft 135 extending outward. The splined shaft 135 may be received in splined receptacle 137 on arm 104 or 106. The splines may be spaced apart at any distance, but in preferred embodiments, the splines are spaced apart so that the waveguide illuminator 120 may be pivoted every 10 degrees, more preferably every 5 degrees, and even more preferably every 2 degrees or every 1 degree. The fit between the splined shaft 135 and the receptacle 137 is tight enough to prevent the splined shaft from falling out, therefore the splined shaft must be pressed in, and pulled out. Additionally, FIG. 1C more clearly illustrates coupling element 134 which has a snap fitting 139 for releasably engaging the waveguide illuminator 120. FIG. 1D is a top view of the exploded view in FIG. 1C. In this or any other embodiments, other mechanisms may be used to allow the waveguide illuminator to be moved in one degree, two degrees, three degrees, or more degrees of freedom. One of skill in the art will appreciate that any number of mechanisms may be used to accomplish this such as with ball joints, hinges, etc. Additionally, the motion in any of these embodiments may be stepped so that movement is in discrete amounts, or the motion may be continuous. A locking mechanism may also be used to hold the waveguide illuminator in position after it has been adjusted into a desired position. Additional exemplary examples are disclosed below.

Figure 2A:
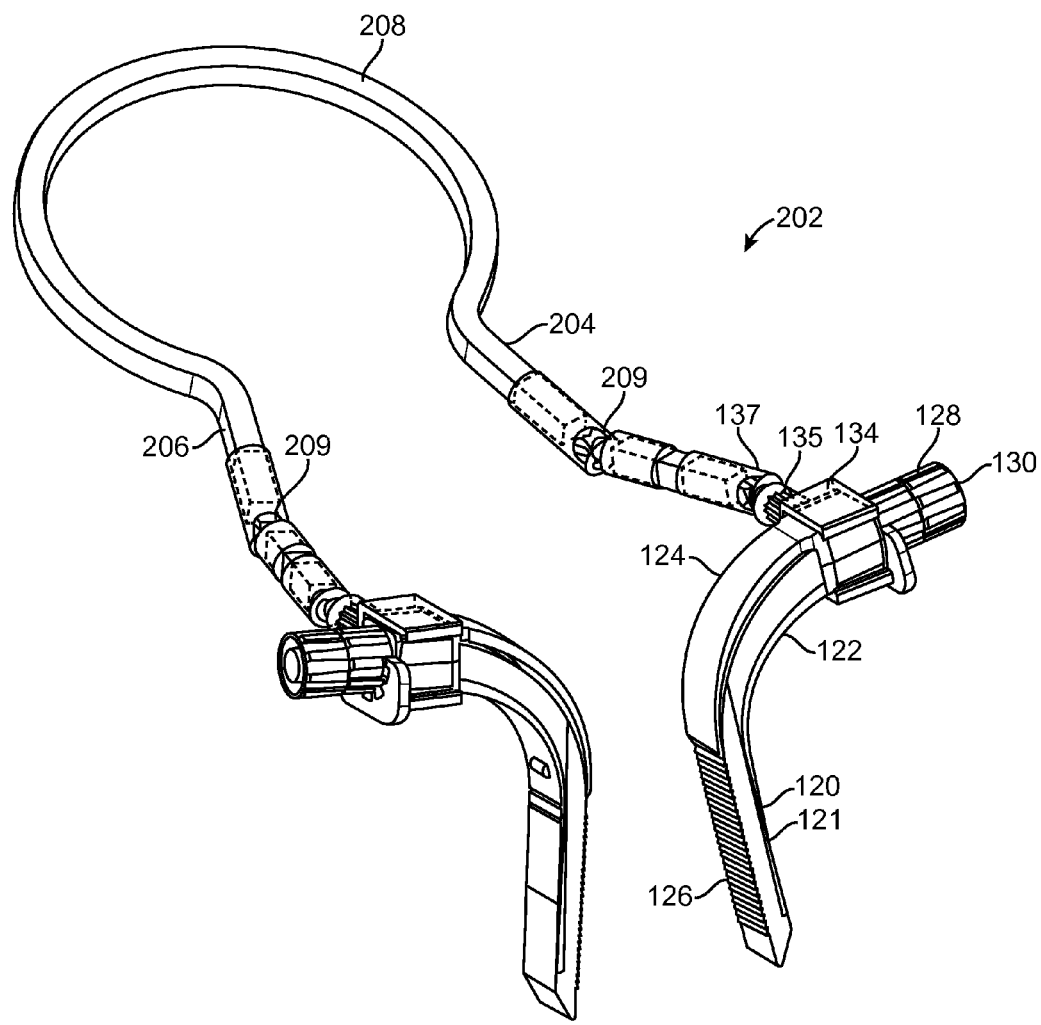
FIG. 2A illustrates a perspective view of another exemplary embodiment of an illuminated clip.
Figure 2B:
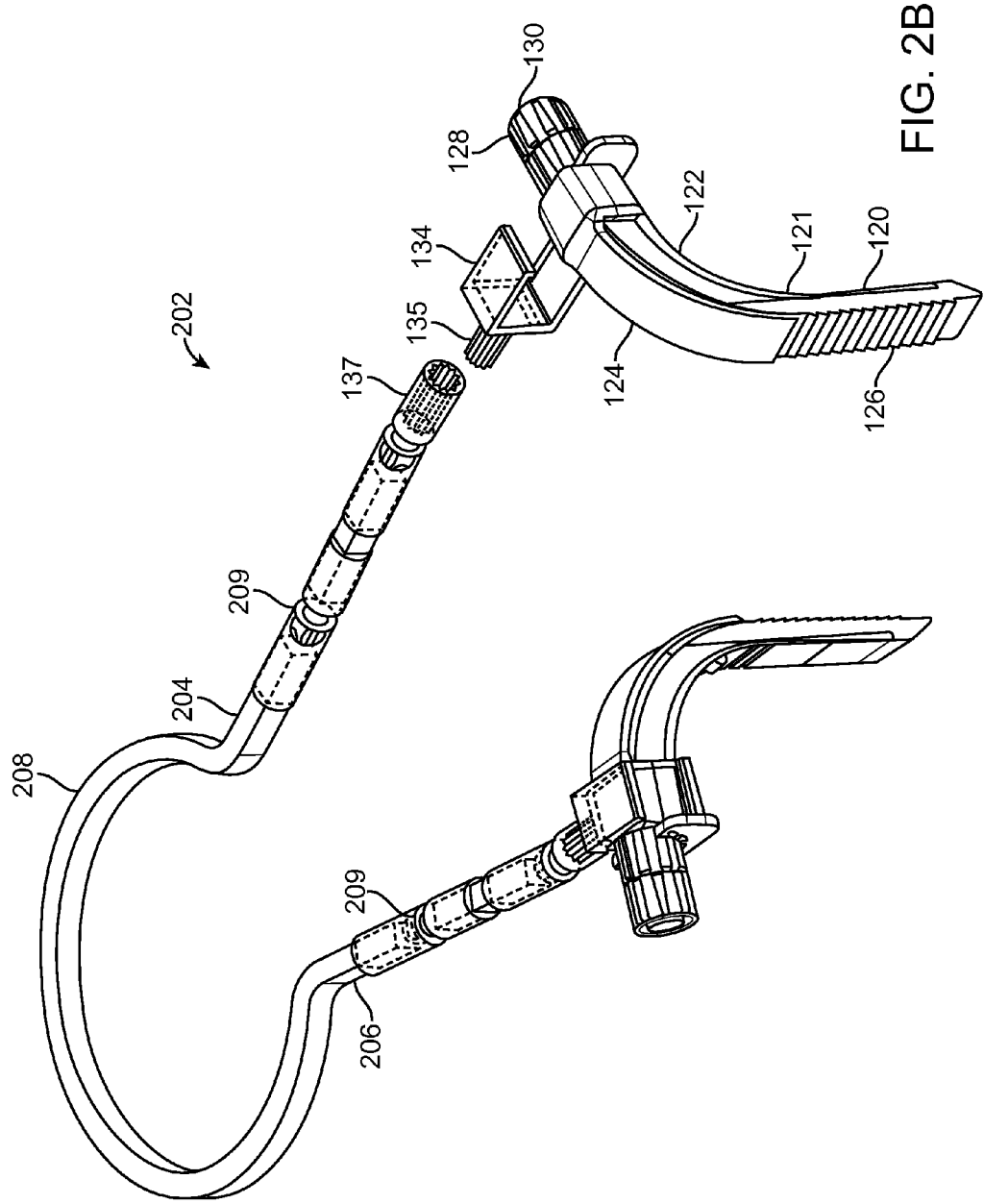
FIG. 2B illustrates a partially exploded view of the embodiment in FIG. 2A.
Figure 2C:
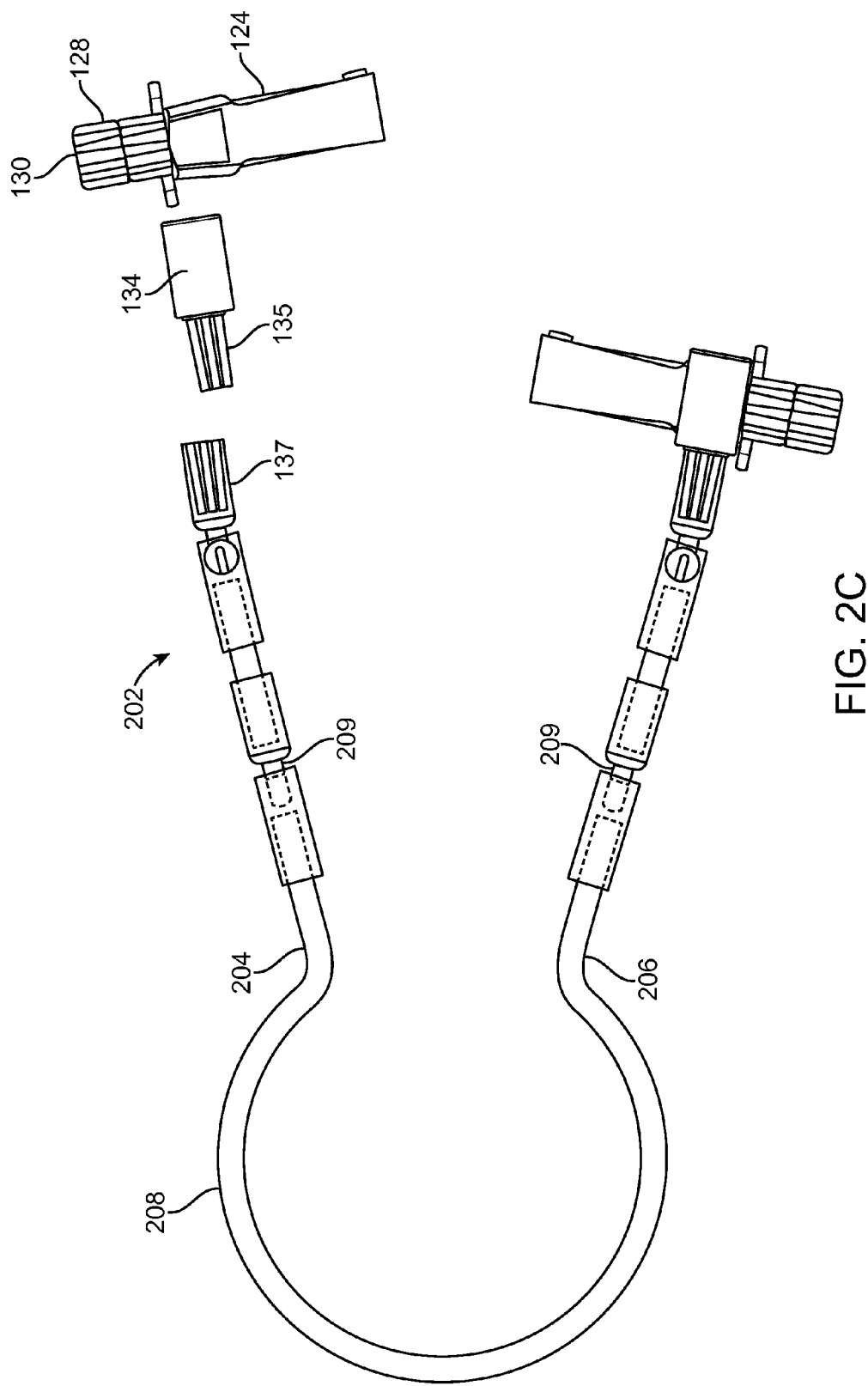
FIG. 2C illustrates a top view of FIG. 2B.

FIGS. 2A-2C illustrate another exemplary embodiment of an illuminated clip. This embodiment is similar to the one previously described above, with the major difference being the geometry of the arms and connector element, and also waveguide illuminator position may be adjusted along additional axes and not just limited to pitch.

FIG. 2A shows the illuminated clip 202 having arms 204, 206 connected together with a connector element 208. The arms may be articulated with a joint 209 so that the waveguide illuminator position may be adjusted. Other aspects of the waveguide illuminator generally take the same form as previously described in FIGS. 1A-1D above.

Arms 204, 206 and connector element 208 have a square cross-section, and therefore the arms in this embodiment are not biased to flex preferentially in one direction. The arms and connector element may be made of similar metals, polymer, or other materials previously disclosed. In addition to adjusting waveguide illuminator 120 pitch (also referred to as toe-in or toe-out) with splined shaft 135 and receptacle 137, a portion of the arms 204, 206 also include an articulating mechanism 209 that allows further adjustment of waveguide illuminator position. In this embodiment, the articulating mechanism is a ball pivot which permits adjustment of the waveguide illuminator in three dimensions.

FIG. 2B illustrates a partially exploded view of the embodiment in FIG. 2A. The splined pin 135 and splined receptacle 137 for adjusting pitch of the waveguide illuminator 120 are more clearly illustrated in this view. FIG. 2C illustrates a top view of the FIG. 2B.

Figure 3A:
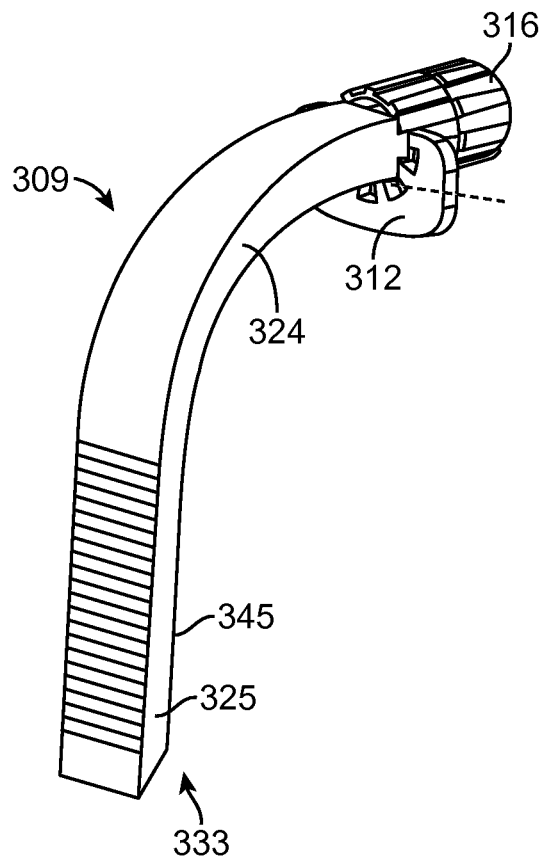
FIG. 3A illustrates a perspective view of an exemplary waveguide illuminator.

FIGS. 3A-3E illustrate an embodiment of the waveguide illuminator that may be used in any of the illuminated clips described above. FIG. 3A more clearly illustrates the waveguide illuminator after it has been disengaged from the spring clip and the front and back shields have been removed for clarity. The waveguide illuminator 309 is a non-fiber optic waveguide preferably injection molded out of a homogenous polymer, and having a single index of refraction. Exemplary polymers include acrylic, polycarbonate, cyclo olefin copolymer and cyclo olefin copolymer. Thus, the waveguide illuminator may be a single monolithic component. A plate 312 is coupled with a proximal end of the waveguide illuminator and acts as a shield to prevent other surgical instruments from damaging the waveguide illuminator, and also may include features that help the waveguide illuminator snap into or otherwise engage the arms of the illuminated clip. Additionally, front and back shields (not illustrated) which have been previously discussed above may be coupled with plate 312 or may be molded integrally as a part of the plate. Plate 312 is also joined to collar 316, and collar 316 is preferably attached to input dead zones 322D (best seen in FIG. 3B), the collar surrounds illumination input 320 which may have a cylindrical cross-section transitioning into a rectangular or square cross-section 322, thereby creating the optical dead zones 322D where there is no light or substantially no light transmitted by total internal reflection. The collar may be attached to the input dead zones 322D by adhesives, ultrasonic welding, press fit, fasteners, solvent bonding, etc. Collar 316 surrounds the cylindrical input 320 and forms an air gap 320G that is circumferentially disposed therearound (best seen in FIG. 3C). The collar preferably only contacts the dead zones 322D (where no light or substantially no light is transmitted by total internal reflection), and there is preferably no contact between the collar and the active zones (where light is transmitted by total internal reflection) of the light input, thereby minimizing light lost. The waveguide illuminator 309 also includes a curved neck portion 324, rear surface 345, output section 325, and output end 333.

Figure 3B:
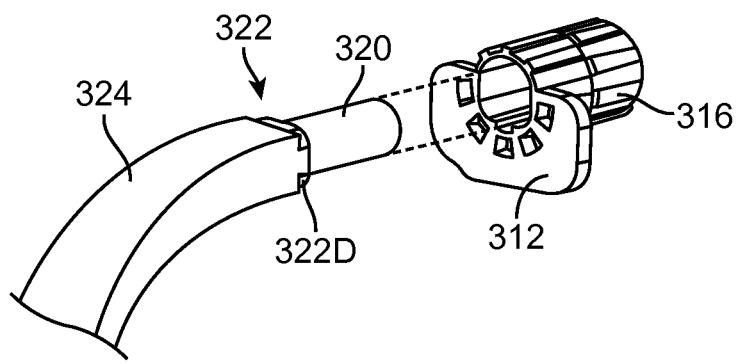
FIG. 3B illustrates a perspective view of the light input end of the waveguide illuminator in FIG. 3A.
Figure 3C:
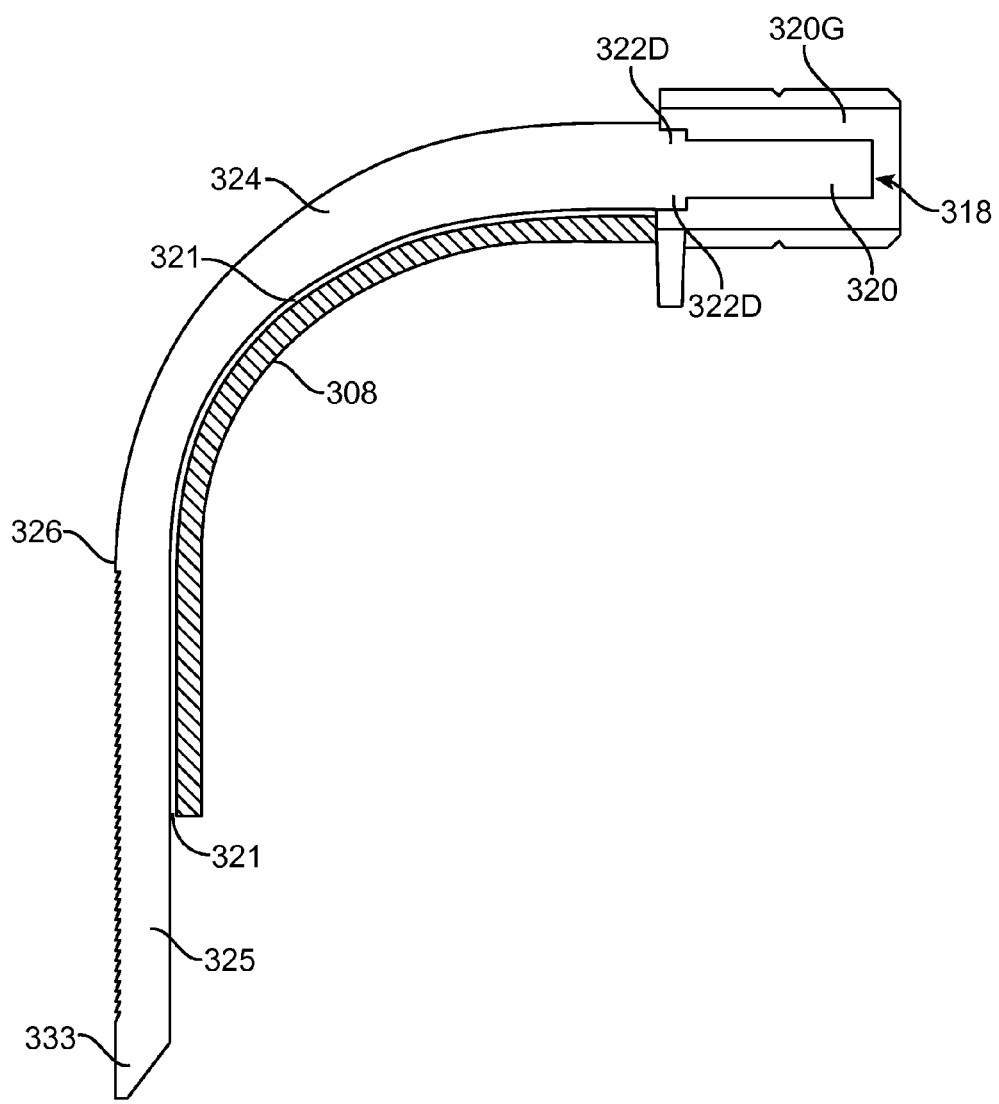
FIG. 3C illustrates a side view of the waveguide illuminator in FIG. 3A.
Figures 3D, 3E:
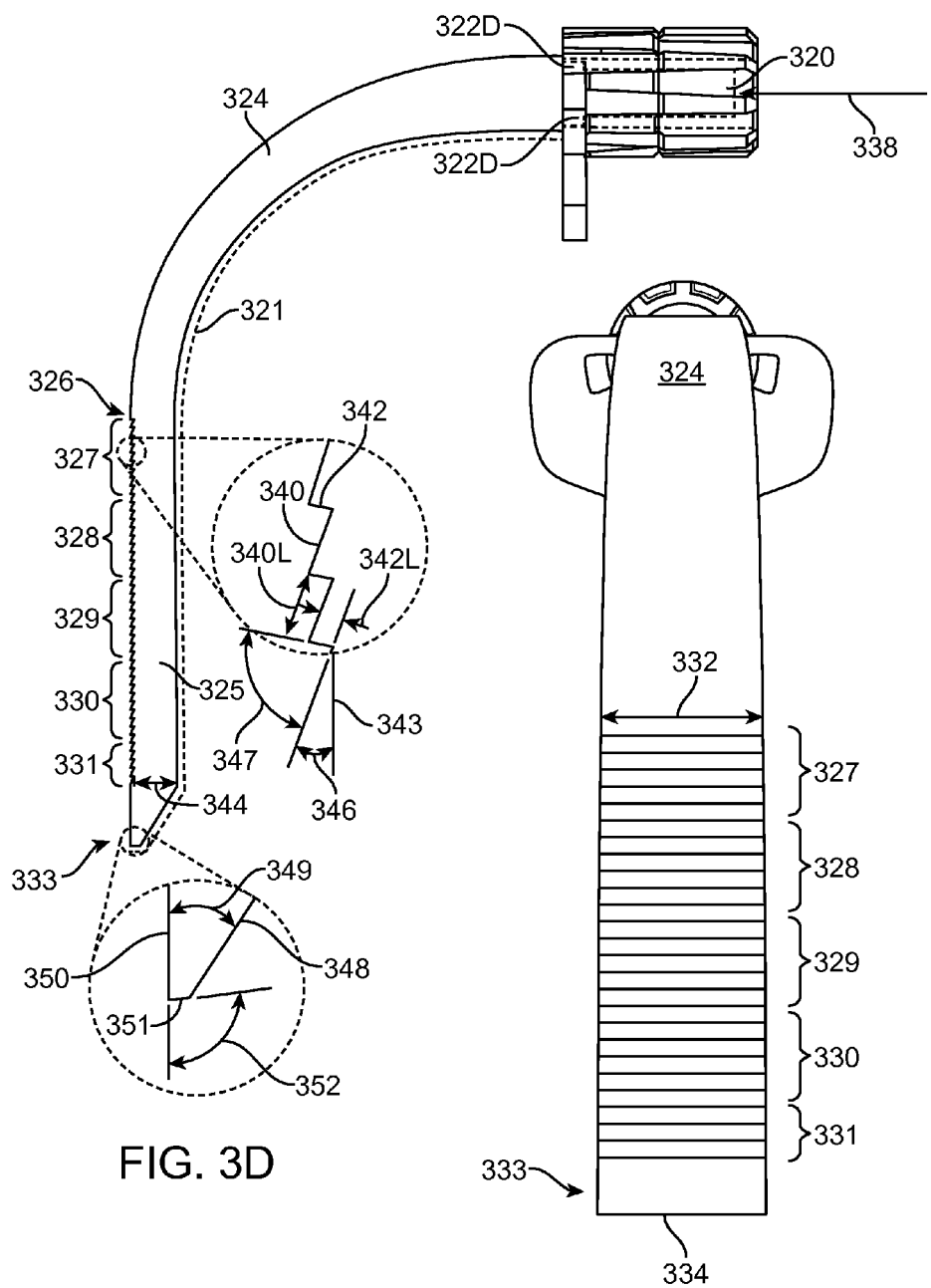
FIG. 3D illustrates a light extraction features on the waveguide illuminator of FIG. 3A.
FIG. 3E illustrates an end view of the light extraction features in FIG. 3D.

The waveguide illuminator 309 is configured to form a series of active zones to control and conduct light from the waveguide illuminator input 318 (best seen in FIG. 3C) of the cylindrical input zone to one or more output zones such as output zones 327 through 331 and output end 333 as seen in FIGS. 3D-3E. Some embodiments of the waveguide illuminator may also include dead zones where no light or substantially no light is transmitted via total internal reflection. The dead zones are idea locations for engagement elements such as standoffs to be disposed in order to help minimize contact between the waveguide and any adjacent structures such as the front shield or back shields discussed above. This also helps maintain an air gap between the front and rear surfaces of the waveguide illuminator and the corresponding front and back shields that may be disposed thereover.

Light is delivered to the waveguide illuminator input 318 along light input path 338 using any conventional mechanism such as a standard ACMI connector preferably having a 0.5 mm gap between the end of the fiber bundle and waveguide illumination 318, which is preferably about 4.2 mm diameter to gather the light from a preferably 3.5 mm fiber bundle with preferably 0.5 NA. Light incident to input 318 enters the illumination blade through generally cylindrical, active input zone 320 and travels through active input transition 322 to a generally rectangular active retractor neck 324 and through output transition 326 (best seen in FIG. 3C) to output portion 325 which contains active output zones 327 through 331 and active output end 333. Neck 324 is generally rectangular and is generally square near input transition 322 and the neck configuration varies to a rectangular cross section near output transition 326. Output 325 has a generally high aspect ratio rectangular cross-section resulting in a generally wide and thin blade. Each zone is arranged to have an output surface area larger than the input surface area, thereby reducing the temperature per unit output area. FIG. 3B highlights the input portion of the waveguide illuminator with the collar 316 removed.

In the illustrated configuration waveguide illuminator 309 includes at least one dead zone, dead zone 322D, generally surrounding input transition 322. An air gap such as air gap 321 is preferably maintained between all active zones on the rear surface of the illumination waveguide and the rear shield 308 as seen in FIG. 3C. A similar air gap is also preferably maintained between active zones of the front surface of the illumination waveguide and the front shield. Neck zone 324 ends with dimension 332 (best seen in FIG. 3E) adjacent to output transition 1326 which extends to dimension 334 at the output zones (best seen in FIG. 3E). The dimensions may be the same or may change in order to create additional dead zones (not illustrated) adjacent to output transition 326. These dead zones are suitable locations for mounting tabs or other engagement elements such as standoffs (not illustrated) to minimize any effects of the engagement elements on the light path.

Output zones 327, 328, 329, 330 and 331 have similar configurations with different dimensions. Referring to the detailed view of FIG. 3D, the characteristics of output zone 327 are illustrated. Each output zone is formed of parallel prism shapes with a primary surface or facet such a primary facet 340 with a length 340L and a secondary surface or facet such as secondary facet 342 having a length 342L. The facets are oriented relative to plane 343 which is parallel to and maintained at a thickness or depth 344 from rear surface 345. In the illustrated configuration, all output zones have the same depth 344 from the rear surface.

The primary facets of each output zone are formed at a primary angle 346 from plane 343. Secondary facets such as facet 342 form a secondary angle 347 relative to primary facets such as primary facet 340. In a preferred embodiment, output zone 327 has primary facet 340 with a length 340L of 0.45 mm at primary angle of 27 degrees and secondary facet 342 with a length 342L of 0.23 mm at secondary angle 88 degrees. Output zone 328 has primary facet 340 with a length 340L of 0.55 mm at primary angle of 26 degrees and secondary facet 342 with a length 342L of 0.24 mm at secondary angle 66 degrees. Output zone 329 has primary facet 340 with a length 340L of 0.53 mm at primary angle of 20 degrees and secondary facet 342 with a length 342L of 0.18 mm at secondary angle 72 degrees. Output zone 330 has primary facet 340 with a length 340L of 0.55 mm at primary angle of 26 degrees and secondary facet 342 with a length 342L of 0.24 mm at secondary angle 66 degrees. Output zone 331 has primary facet 340 with a length 340L of 0.54 mm at primary angle of 27 degrees and secondary facet 342 with a length 342L of 0.24 mm at secondary angle 68 degrees. Thus, the primary facet 340 in preferred embodiments forms an acute angle relative to the plane in which the rear surface 345 lies, and the secondary facet 342 in preferred embodiments forms an obtuse angle relative to the plane in which the rear surface 345 lies. These preferred angles allow light to be extracted from the waveguide illuminator so that light exits laterally and distally toward the surgical field in an efficient manner, and this configuration also allows the waveguide illuminator to be injection molded and easily ejected from the mold. Other angles are possible, as will be appreciated by one of skill in the art.

Output end 333 is the final active zone in the waveguide illuminator and is illustrated in detail in FIG. 3D. Rear reflector 348 forms angle 349 relative to front surface 350. Front surface 350 is parallel to rear surface 345. Terminal facet 351 forms angle 352 relative to front surface 350. In the illustrated configuration, angle 349 is preferably 32 degrees and angle 352 is preferably 95 degrees. This distal tip geometry helps to prevent light from reflecting back proximally toward the physician, thereby helping to prevent glare.

Other suitable configurations of output structures may be adopted in one or more output zones. For example, output zones 327 and 328 might adopt a concave curve down and output zone 329 might remain generally horizontal and output zones 330 and 331 might adopt a concave curve up. Alternatively, the plane at the inside of the output structures, plane 343 might be a spherical section with a large radius of curvature. Plane 343 may also adopt sinusoidal or other complex geometries. The geometries may be applied in both the horizontal and the vertical direction to form compound surfaces.

In other configurations, output zones may provide illumination at two or more levels throughout a surgical site. For example, output zones 327 and 328 might cooperate to illuminate a first surgical area and output zones 329 and 330 may cooperatively illuminate a second surgical area and output zone 331 and output end 333 may illuminate a third surgical area. This configuration eliminates the need to reorient the illumination elements during a surgical procedure.

Figure 8:
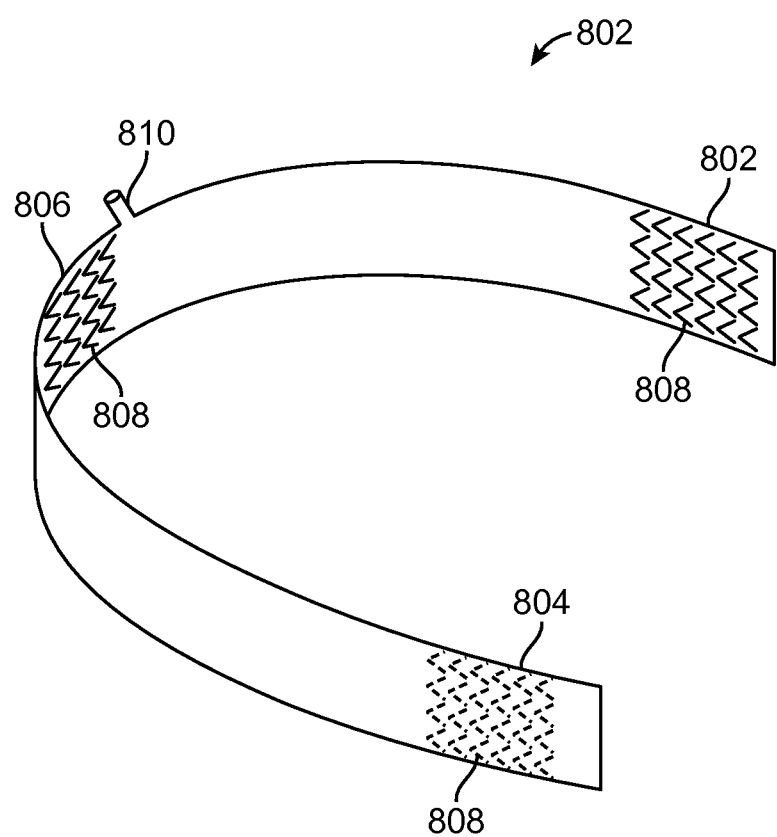
FIG. 8 illustrates an alternative embodiment of an illuminated clip.

FIG. 8 illustrates an alternative embodiment of an illuminated clip. Instead of coupling a separate optical waveguide to the arms of the clip, in this embodiment the optical waveguide is integrated and formed into the clip. Thus, illuminated clip 802 includes a pair of arms 802, 804 coupled together with a connector element 806. The connector element in this embodiment is a U-shaped connector. The clip is fabricated from an optical polymer to form an optical waveguide using materials such as polycarbonate, acrylic, silicone, cyclo olefin polymer, cyclo olefin copolymer, or other polymers known in the art. The arms and/or connector element are resilient enough so that the arms of the clip may be deflected inward and outward during use without breaking. Light input 810 is coupled with the optical waveguide and may include a standard optical coupling such as an ACMI connector in order to allow the optical waveguide to be coupled with an external light source. In alternative embodiments, the light input 810 may be a fiber optic input that is integral with the waveguide clip. Thus, input 810 may be insert molded, bonded, or otherwise integrally coupled to the waveguide clip. This integral light input may sometimes be referred to as a pigtail connector. Light is then delivered from the light source to the light input 810 and then delivered along the arms of the illuminated clip. Light extraction features 808 such as prisms, lenses, facets, microstructures may be disposed anywhere along the illuminated clip in order to extract and deliver light to the surgical field. Optical films applied to the waveguide may also be used to extract and direct the light. Exemplary light extraction features are discloses elsewhere in this specification.

Figure 4A:
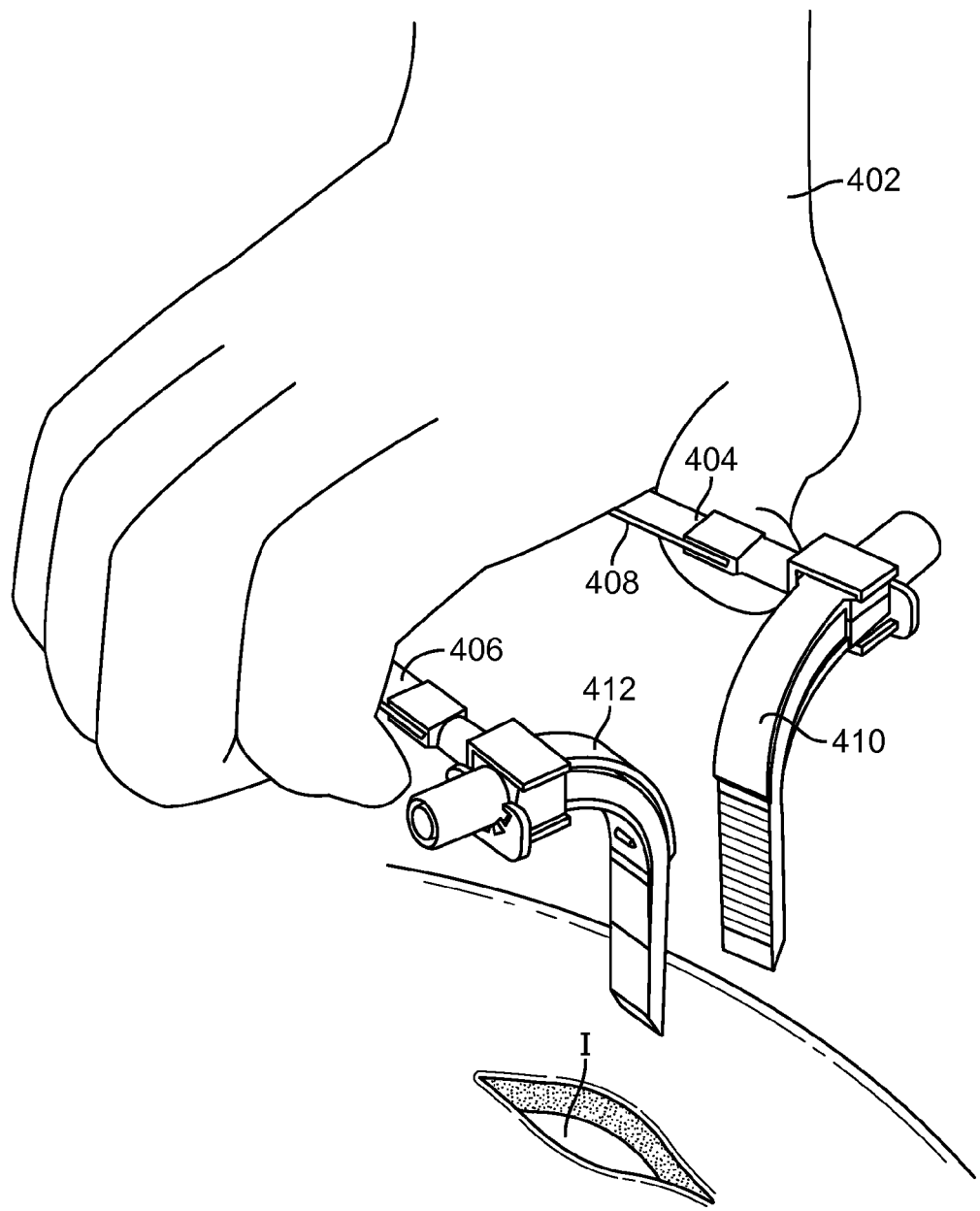
FIGS. 4A-4E illustrate an exemplary method of using the illuminated clip.

FIGS. 4A-4E illustrate an exemplary use of the illuminated clip described herein. In FIG. 4A, an operator such as a surgeon or physician's assistant may use his hand 402 to grasp the illuminated clip 408 and advance it toward a surgical incision I. The illuminated clip 408 may be any of the embodiments described herein. The surgeon may grasp the illuminated clip along the arms 404, 406 or the waveguide illuminators 410, 412 may also be grasped.

Figure 4B:
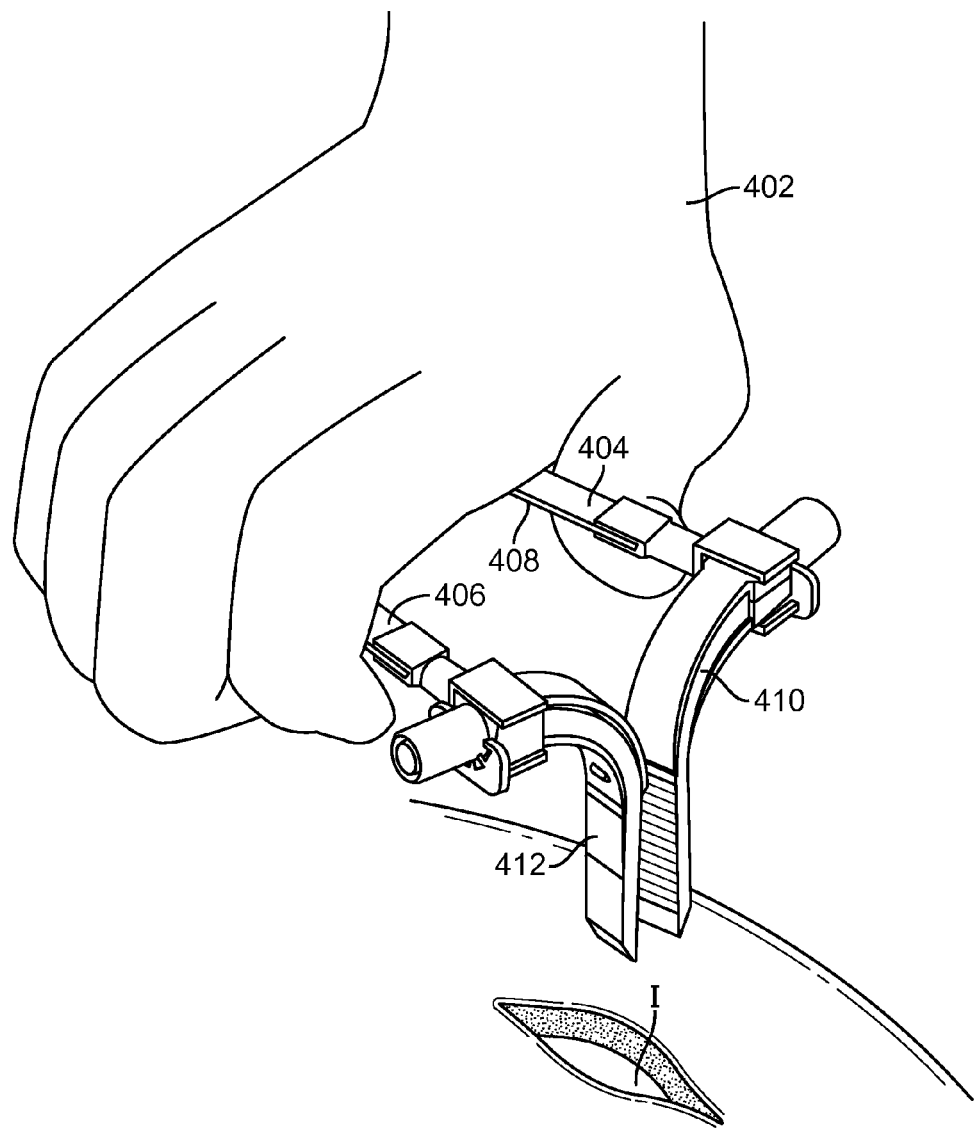
Figure 4C:
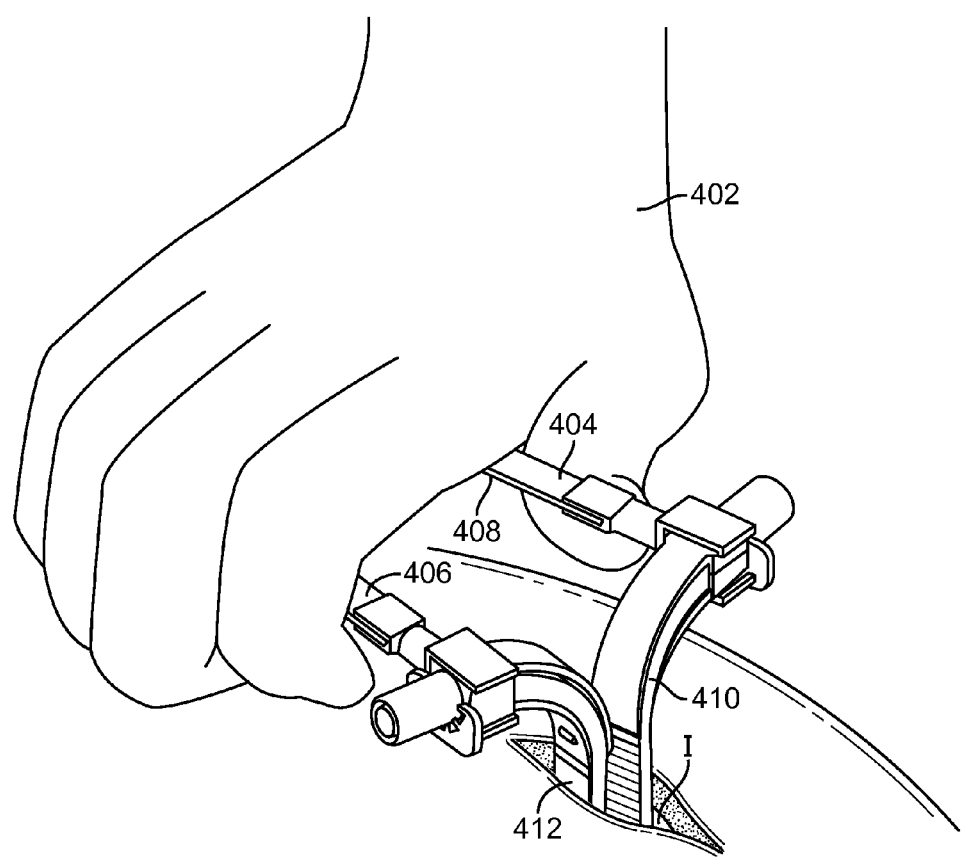
Figure 4D:
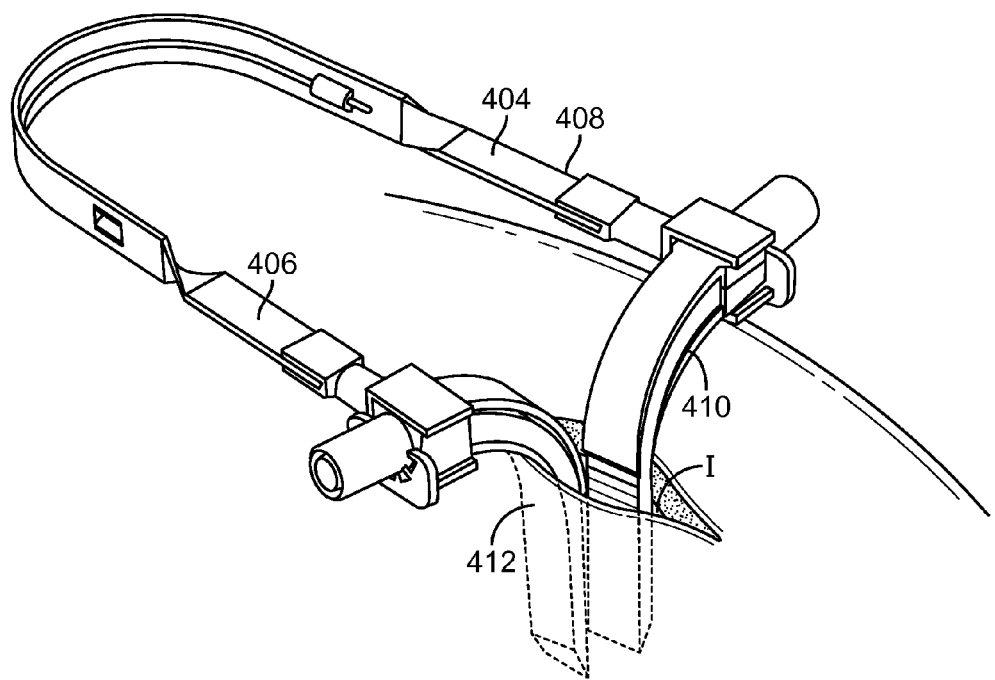
Figure 4E:
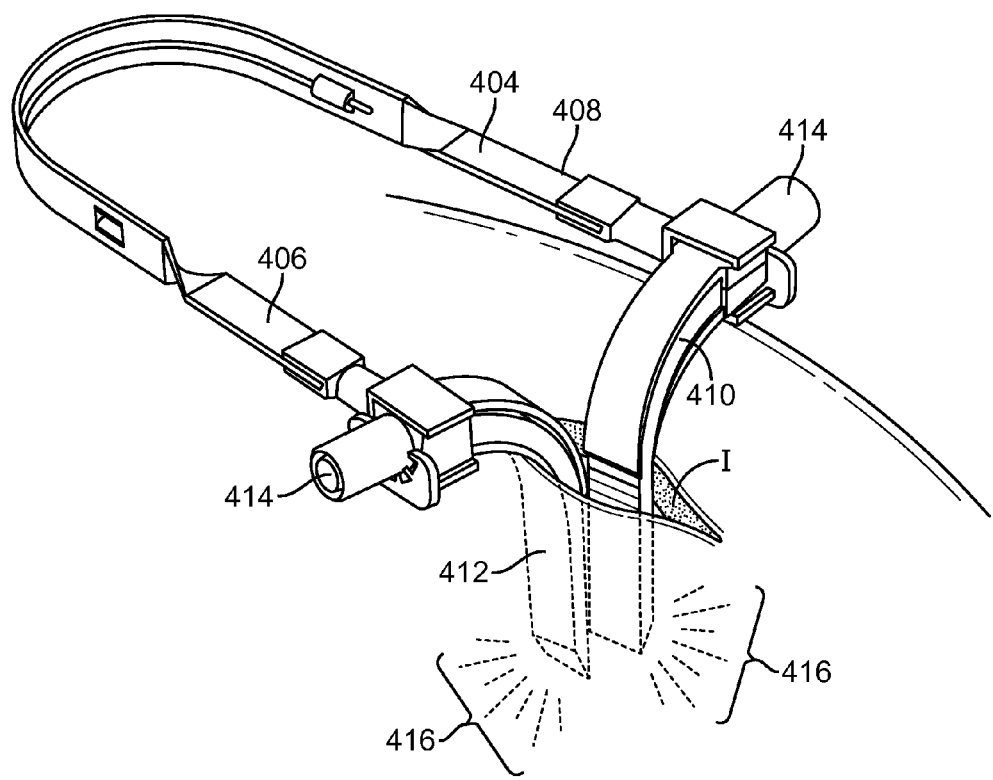

In FIG. 4B the surgeon squeezes or otherwise applies an inward force to arms 404, 406 to collapse the arms laterally inward so that the waveguide illuminators 410, 412 collapse inward toward one another, thereby reducing profile. In the collapsed configuration, the surgeon may then insert the waveguide illuminators 410, 412 into the incision I as seen in FIG. 4C. Once positioned, the surgeon may release the illuminated clip 408 from his grasp, thereby allowing the arms 404, 406 to spring laterally outward and return to their biased expanded configuration as seen in FIG. 4D. This engages the rear surfaces of the waveguide illuminator with the tissue in the incision thereby seating the clip in the incision. The spring force of the clip is adequate enough so that the clip then seats itself in the incision without undesirably moving around. Additionally, in preferred embodiments, the spring clip expands outward with only enough force to seat the clip, but without enough force to further retract the tissue. In still other embodiments, the spring force may be sufficiently high enough to not only seat the illuminated clip, but also to retract tissue. The arms and connector element of the clip will generally remain on an outer surface such as a fenestrated drape on top of the patient. In other embodiments, some or all of the arms and connector element may be disposed in the incision, depending on how large the incision is and how large the illuminated clip is. Once properly positioned, an illumination source (not illustrated) may be optically coupled with the light input portion 414 of each waveguide illuminator 410, 412 thereby allowing light to be delivered to the waveguide. The light travels through the waveguide illuminator by total internal reflection and then the light is extracted from the waveguide with surface features such as microstructures, facets, or lenses, as previously described above, in order to deliver light 416 to illuminate the incision I and surgical field, as seen in FIG. 4E. Upon completion of the surgical procedure, the surgeon may grasp the arms again and squeeze them to reduce profile of the clip and then it may be removed from the incision.

Figure 5:
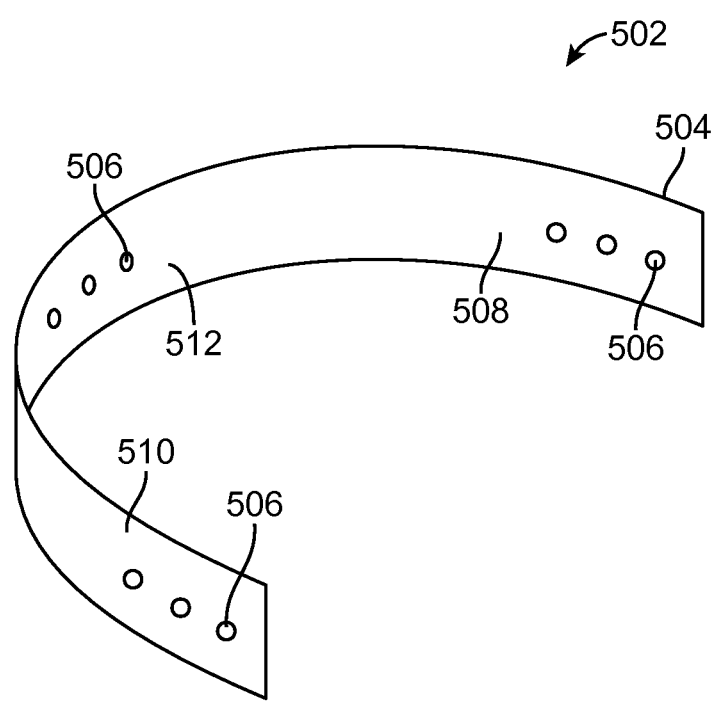
FIG. 5 illustrates another exemplary embodiment of an illuminated clip.

FIG. 5 illustrates another embodiment of an illuminated clip 502. The illuminated clip is similar to previous embodiments with the major difference being that instead of optical waveguides coupled to the arms of the clips, light emitting diodes (LEDs) are used instead. Illuminated clip 502 includes a pair of arms 508, 510 connected together with a U-shaped coupling element 512. One or more LEDs 506 may be attached to one arm, both arms, the coupling element, or anywhere along the illuminated clip. Wires may couple the LEDs with a battery coupled with the arms or coupling element, or the power source may be external such as a remote battery, or house mains. The LEDs may also be adjustably positioned along the illuminated clip so that the illumination pattern can be adjusted. Other aspects of the illuminated clips previously described above may also be used with this embodiment, such as including pivoting mechanisms on the arms in order to pivot the LEDs inward or outward. Use of the LED illuminated clip is generally the same as previously described above.

Figure 6:
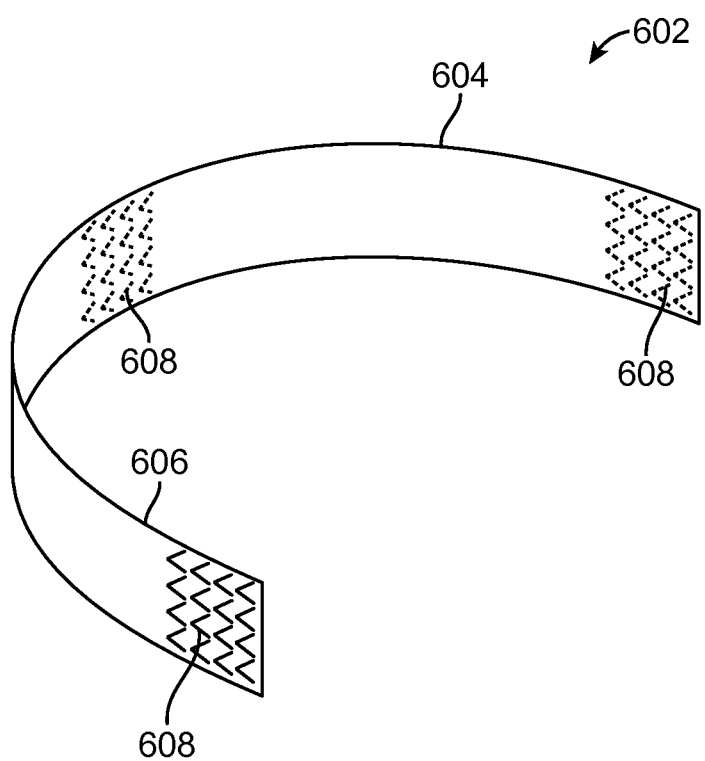
FIG. 6 illustrates the use of anchoring elements on the illuminated clip.

In order to help secure the illuminated clip to tissue, it may be advantageous to include one or more anchoring elements on the device. FIG. 6 illustrates an exemplary embodiment of an illuminated clip 602 with anchoring elements. The anchoring elements may be used with any of the illuminated clips described herein. Anchoring elements 608 may be disposed on the tissue contacting surface of the clip (outer surface in this embodiment) and the anchoring elements may be disposed near the ends of the arms 604, 604, and they may also be included anywhere along the clip including the connector element that joins the arms together. The anchoring elements may include teeth, barbs, raised structures, or any other means that helps the clip to engage the tissue and prevent the clip from slipping out of position.

Figure 7:
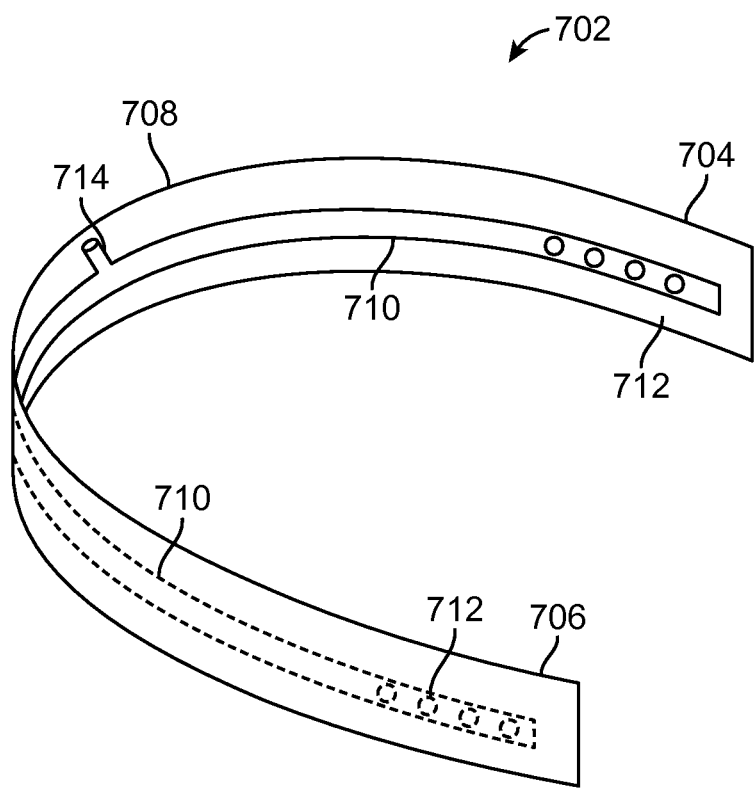
FIG. 7 illustrates an illuminated clip with suction.

In some embodiments it may be desirable for the illuminated clip to be able to evacuate smoke or other fumes from the surgical site. Smoke is often generated during surgery due to the use of electrosurgical instruments. FIG. 7 illustrates an exemplary embodiment of an illuminated clip 702 that can evacuate smoke. The illuminated clip 702 may be any of the illuminated clips described herein and includes a suction tube 710 coupled to the arms 704, 706 and connector element 708. The suction tube 710 is preferably coupled to an inside surface of the illuminated clip but could be disposed on any surface. The suction tube 710 has suction holes 712 near the ends of the arms 704, 706. When a vacuum is applied to the suction tube, smoke or other fumes will be drawn into the suction holes 712. A vacuum line may be coupled to the suction tube 710 using connector 714. Additionally, the suction holes 712 may be disposed along any portion of the suction tube including the portion adjacent the connector element 708. In alternative embodiments, the suction tube may be substituted with a channel in the arms of the illuminated clip. A cover may be placed over the channel so that suction is maintained, and the cover may have suction holes.

Figure 9:
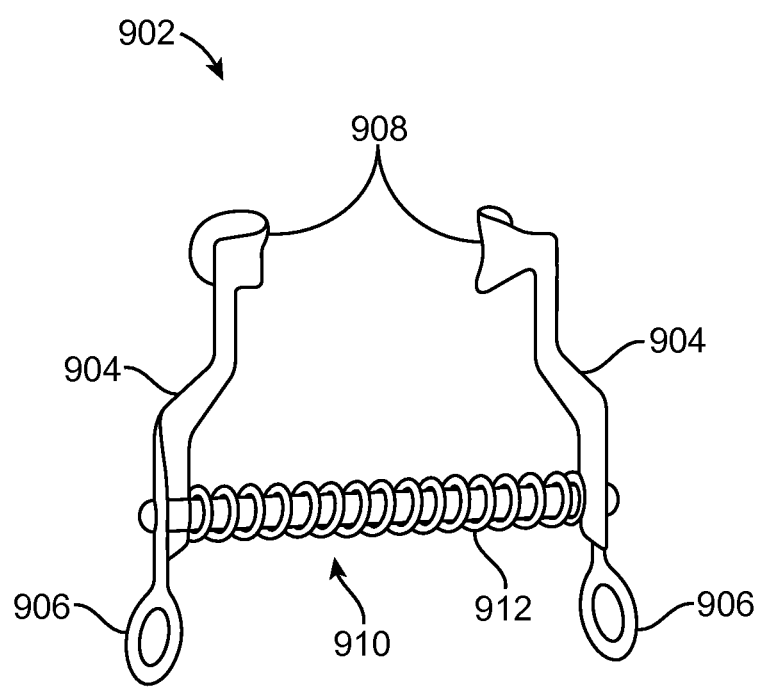
FIG. 9 illustrates another embodiment of an illuminated clip.

FIG. 9 illustrates still another exemplary embodiment of an illuminated clip 902. The clip 902 includes a pair of opposed arms 904 coupled together to slide over a spring 912 loaded bar 910. One end of the arms includes a handle 906 or finger grasping feature 906 to facilitate actuation by the user. The other end of the arms includes a blade 908. In this embodiment, the blades are curved to grasp tissue. Any of the waveguides or light sources described herein may be coupled to the blades or other portions of the clip to illuminate the surgical field. In this embodiment, the arms are actuated by the user and move linearly inward and outward relative to one another along bar 910. This is unlike some of the other spring clips described herein where the arms bend inward or outward in an arc or pivot relative to one another. In the present embodiment, the arms move parallel relative to one another. Linear movement of the arms may be desirable when inserting the clip into certain incisions and adjusting it to fit the anatomy. Additionally, the linear movement allows light from waveguides on both blades to be adjusted to illuminate in a parallel fashion, or to be pointed directly toward one another which may be desirable when illuminating a surgical field, unlike some of the other embodiments previously described where light from two opposed waveguides on opposed clip arms will be angled relative to one another. The clip may be opened enough to just seat the clip in the incision and illuminate the surgical field, or the clip may be opened and retract tissue. The spring 910 may have any spring constant in order to provide the desired force and it may be biased to keep the clip closed or open as desired.

FIGS. 10A-10B illustrate yet another exemplary embodiment of an illuminated clip 1002. The clip 1002 includes two actuatable arms 1004 having blades 1006 attached at one end, and the opposite end of the arms are coupled together with an adjustable locking mechanism that includes a ratchet 1016, a pawl 1018, and a lever 1014 for actuating the pawl 1018. The lever may be spring loaded so that the arm extends radially outward thereby biasing the pawl into a locked position with the ratchet. Pressing the lever inward, releases the pawl thereby allowing the ratchet to move and thus the two arms can pivot inward or outward relative to one another. The blades on the clip may be screwed in position and loosening of the screw 1008 may allow adjustment of the blade position relative to the arms. Additionally, the blades may have a curved J-shaped in order to engage tissue, and engagement features such as slots 1012 may also help capture tissue and prevent the blades from slipping. Other engagement features or anti slip features include holes, bumps, texturing, cutouts, etc. Any waveguide or illumination source disclosed herein may be coupled to the blades or other portions of the device to illuminate the surgical field. The clip may be opened just enough to seat the clip in the incision, or the clip may be opened up even wider to retract tissue in the incision.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A surgical clip for illuminating tissue in a surgical field, said surgical clip comprising:
a first elongate arm;
a second elongate arm;
a connector element joining the first and second elongate arms, wherein the arms are biased to expand laterally outward into an expanded configuration, wherein in the expanded configuration the first and second arms expand into engagement with the tissue in the surgical field with enough force to seat the clip without retracting the tissue; and
a waveguide illuminator coupled to the first arm, wherein the waveguide illuminator has a light input portion, a light output portion, and a light conducting portion extending between the light input portion and the light output portion, and wherein light passes through the waveguide illuminator by total internal reflection, and wherein the waveguide illuminator directs light to the tissue in the surgical field.

2. The surgical clip of claim 1, wherein the first arm has a proximal portion and a distal portion, wherein the proximal portion is biased to preferentially flex in a first direction, and wherein the distal portion is biased to preferentially flex in a second direction transverse to the first direction.

3. The surgical clip of claim 2, wherein the proximal portion is twisted relative to the distal portion.

4. The surgical clip of claim 1, further comprising a waveguide connector element coupled to the first arm, wherein the waveguide connector element releasably couples the waveguide illuminator to the first arm.

5. The surgical clip of claim 4, wherein the waveguide connector element comprises a snap fitting.

6. The surgical clip of claim 1, wherein the first arm comprises a pivoting mechanism for adjusting pitch of the waveguide illuminator.

7. The surgical clip of claim 6, wherein the pivoting mechanism comprises a splined shaft operatively coupled to one of the first arm or the waveguide illuminator, and a receptacle for receiving the splined shaft operatively coupled with the other of the first arm or the waveguide illuminator.

8. The surgical clip of claim 1, wherein the second arm has a proximal portion and a distal portion, wherein the proximal portion is biased to preferentially flex in a first direction, and wherein the distal portion is biased to preferentially flex in a second direction transverse to the first direction.

9. The surgical clip of claim 8, wherein the proximal portion is twisted relative to the distal portion.

10. The surgical clip of claim 1, further comprising a second waveguide illuminator and a waveguide connector element coupled to the second arm, wherein the waveguide connector element releasably couples the second waveguide illuminator to the second arm.

11. The surgical clip of claim 10, wherein the waveguide connector element comprises a snap fitting.

12. The surgical clip of claim 1, further comprising a second waveguide illuminator coupled to the second arm, and wherein the second arm comprises a pivoting mechanism for adjusting pitch of the second waveguide illuminator.

13. The surgical clip of claim 12, wherein the pivoting mechanism comprises a splined shaft operatively coupled to one of the second arm or the second waveguide illuminator, and a receptacle for receiving the splined shaft operatively coupled with the other of the second arm or the second waveguide illuminator.

14. The surgical clip of claim 1, wherein the connector element comprises a U-shaped element.

15. The surgical clip of claim 1, wherein the connector element comprises a spring.

16. The surgical clip of claim 1, wherein the waveguide illuminator comprises a shield disposed thereover, the shield adapted to prevent glare from shining back into a physician's eyes, and the shield adapted to prevent scratching or damage to the waveguide by other surgical instruments.

17. The surgical clip of claim 16, wherein the shield further comprises a collar, the collar disposed around the light input portion of the waveguide illuminator with an air gap therebetween, the air gap circumferentially disposed around the light input portion of the waveguide illuminator.

18. The surgical clip of claim 1, further comprising a backing element, the backing element coupled to the waveguide illuminator such that an air gap is disposed therebetween, and wherein the backing element is adapted to reduce or prevent tissue or body fluids from contacting a rear surface of the waveguide illuminator.

19. The surgical clip of claim 1, wherein the waveguide illuminator comprises active zones and dead zones, wherein light passes through the active zones by total internal reflection, and wherein substantially no light passes through the dead zones by total internal reflection.

20. The surgical clip of claim 1, wherein the light input portion of the waveguide comprises active zones and dead zones, wherein light passes through the active zones by total internal reflection, and wherein substantially no light passes through the dead zones by total internal reflection.

21. The surgical clip of claim 1, wherein the light input portion comprises a cylindrical proximal portion adapted to be coupled with a light source, and a rectangular distal portion optically coupled with the light conducting portion of the waveguide.

22. The surgical clip of claim 1, wherein the light output portion of the waveguide illuminator comprises a plurality of surface features for extracting light from the waveguide illuminator and directing the extracted light laterally or distally toward the tissue in the surgical field.

23. The surgical clip of claim 1, wherein the surface features comprise parallel prism shapes with a primary facet and a secondary facet.

24. The surgical clip of claim 1, further comprising a spring coupled with the connector element, wherein the spring is biased to expand laterally outward, and wherein the spring facilitates expansion of the first and second arms laterally outward away from one another.

25. The surgical clip of claim 24, further comprising an engagement element coupled with the first arm, the second arm, or with the connector element, and wherein the engagement element captures the spring.

26. The surgical clip of claim 25, wherein the engagement element comprises a central channel extending at least partially therethrough, the central channel sized to receive the spring.

27. The surgical clip of claim 1, further comprising one or more anchoring elements coupled to either the first or the second elongate arm.

28. The surgical clip of claim 27, wherein the anchoring elements comprise teeth.

29. The surgical clip of claim 1, further comprising means for evacuating smoke or fumes from the surgical field.

30. The surgical clip of claim 29, wherein the means for evacuating smoke comprises a suction tube.

31. The surgical clip of claim 1, further comprising a locking mechanism for locking the first and second arms into a desired position relative to one another.

32. The surgical clip of claim 1, wherein the first arm moves parallel relative to the second arm.

33. A method of illuminating a surgical field, said method comprising:
providing a clip having a first arm, a second arm and a waveguide illuminator coupled to the first arm or the second arm;
applying a force to one or more of the first and second arms to move the arms laterally inward toward one another into a collapsed configuration;
positioning the clip while in the collapsed configuration into the surgical field;
releasing the force from the one or more arms thereby allowing the arms to move laterally outward into an expanded configuration, wherein in the expanded configuration the arms engage tissue in the surgical field;
seating the clip in the surgical field; and
illuminating the surgical field with light extracted from the waveguide illuminator.

34. The method of claim 33, wherein the waveguide illuminator has a light input portion, a light output portion, and a light conducting portion extending between the light input portion and the light output portion, and wherein light passes through the waveguide illuminator by total internal reflection, and wherein the waveguide illuminator directs light to the tissue in the surgical field.

35. The method of claim 34, wherein the light input portion of the waveguide comprises active zones and dead zones, wherein light passes through the active zones by total internal reflection, and wherein substantially no light passes through the dead zones by total internal reflection.

36. The method of claim 33, wherein applying the force comprises pressing the first and second arms inward toward one another.

37. The method of claim 36, wherein the first and second arms move parallel to one another.

38. The method of claim 33, wherein positioning the clip comprises advancing the clip into the surgical field.

39. The method of claim 33, wherein releasing the force comprises releasing the first or the second arm from an operator's grasp.

40. The method of claim 33, wherein seating the clip comprises engaging the arms of the clip against tissue in the surgical field so the clip remains stationary and without retracting the tissue.

41. The method of claim 33, wherein illuminating the surgical field comprises extracting light from the waveguide illuminator with a plurality of surface features on the waveguide illuminator and directing the extracted light laterally or distally toward the surgical field.

42. The method of claim 33, further comprising releasably engaging the waveguide illuminator with the first or second arm.

43. The method of claim 33, further comprising detaching the waveguide illuminator from the first or second arm.

44. The method of claim 33, further comprising adjusting pitch of the waveguide illuminator relative to the first or second arm.

45. The method of claim 33, further comprising anchoring the clip in the surgical field.

46. The method of claim 45, wherein anchoring the clip comprises anchoring teeth into the tissue.

47. The method of claim 33, further comprising evacuating smoke or fumes from the surgical field.

48. The method of claim 33, further comprising locking the clip so that the first arm maintains its position relative to the second arm.

49. A surgical clip for illuminating tissue in a surgical field, said surgical clip comprising:
- a first elongate arm;
- a second elongate arm;
- a connector element joining the first and second elongate arms, wherein the arms are biased to expand laterally outward into an expanded configuration, wherein in the expanded configuration the first and second arms expand into engagement with the tissue in the surgical field with enough force to seat the clip without retracting the tissue; and
- one or more lights coupled to the first elongate arm or the second elongate arm, wherein the lights illuminate the surgical field.

50. The surgical clip of claim 49, wherein the light comprise LEDs.

51. The surgical clip of claim 49, further comprising one or more anchoring elements coupled to either the first or the second elongate arm.

52. The surgical clip of claim 51, wherein the anchoring elements comprise teeth.

53. The surgical clip of claim 49, further comprising means for evacuating smoke or fumes from the surgical field.

54. The surgical clip of claim 53, wherein the means for evacuating smoke comprises a suction tube.

55. A surgical clip for illuminating tissue in a surgical field, said surgical clip comprising:
- a first elongate arm;
- a second elongate arm;
- a connector element joining the first and second elongate arms, wherein the arms are biased to expand laterally outward into an expanded configuration, wherein in the expanded configuration the first and second arms expand into engagement with the tissue in the surgical field with enough force to seat the clip without retracting the tissue,
- wherein the construct of the first elongate arm, the second elongate arm and the connector element form an optical waveguide, and
- wherein the first elongate arm or the second elongate arm comprise light extraction structures for extracting light therefrom and for directing light to the surgical field, and
- wherein the optical waveguide is formed from a single homogenous material, and
- wherein light is transmitted through the optical waveguide by total internal reflection.

* * * * *